(12) United States Patent
Hirata et al.

(10) Patent No.: US 10,065,982 B2
(45) Date of Patent: Sep. 4, 2018

(54) HIGH-PURITY ACID-FORM SOPHOROLIPID (SL) CONTAINING COMPOSITION AND PROCESS FOR PREPARING SAME

(71) Applicant: Saraya Co., Ltd., Osaka-Shi (JP)

(72) Inventors: Yoshihiko Hirata, Kashiwara (JP); Mizuyuki Ryu, Kashiwara (JP); Hitoshi Ito, Kashiwara (JP); Michiaki Araki, Kashiwara (JP)

(73) Assignee: Saraya Co., Ltd., Osaka-Shi (JP)

( * ) Notice: Subject to any disclaimer, the term of this patent is extended or adjusted under 35 U.S.C. 154(b) by 39 days.

(21) Appl. No.: 14/382,480

(22) PCT Filed: Mar. 1, 2013

(86) PCT No.: PCT/JP2013/055740
§ 371 (c)(1),
(2) Date: Sep. 2, 2014

(87) PCT Pub. No.: WO2013/129667
PCT Pub. Date: Sep. 6, 2013

(65) Prior Publication Data
US 2015/0112049 A1   Apr. 23, 2015

(30) Foreign Application Priority Data

Mar. 2, 2012 (JP) ................................. 2012-047409

(51) Int. Cl.
| C07H 15/10 | (2006.01) |
| C07H 15/04 | (2006.01) |
| A61Q 19/00 | (2006.01) |
| A61K 8/60 | (2006.01) |
| A23L 29/10 | (2016.01) |
| A23L 33/12 | (2016.01) |

(52) U.S. Cl.
CPC .............. *C07H 15/10* (2013.01); *A23L 29/10* (2016.08); *A23L 33/12* (2016.08); *A61K 8/602* (2013.01); *A61Q 19/00* (2013.01); *C07H 15/04* (2013.01); *A61K 2800/10* (2013.01)

(58) Field of Classification Search
None
See application file for complete search history.

(56) References Cited

U.S. PATENT DOCUMENTS

| 5,756,471 | A | 5/1998 | Hillion | |
| 5,981,497 | A | 11/1999 | Maingault | |
| 6,057,302 | A * | 5/2000 | Borzeix | A61K 8/602 514/25 |
| 2004/0171512 | A1 | 9/2004 | Furuta et al. | |
| 2011/0237531 | A1 | 9/2011 | Yanagisawa | |
| 2012/0142621 | A1 * | 6/2012 | Falus | A61K 31/7028 514/31 |
| 2012/0220464 | A1 | 8/2012 | Giessler-Blank et al. | |
| 2013/0035403 | A1 * | 2/2013 | Schaffer | A61K 31/704 514/777 |

FOREIGN PATENT DOCUMENTS

| EP | 0499434 A1 | 8/1992 |
| EP | 2351847 A1 | 8/2011 |
| JP | 07-118284 A | 5/1995 |
| JP | H10-501260 A | 2/1998 |
| JP | H11-508549 A | 7/1999 |
| JP | 2002-045195 | 2/2002 |
| JP | 2003-009896 | 1/2003 |
| JP | 2003-013093 A | 1/2003 |
| JP | 2006-070231 A | 3/2006 |
| JP | 2008-247845 | 10/2008 |
| JP | 2009-062288 | 3/2009 |
| JP | 2009-531310 A | 9/2009 |
| JP | 2009-275145 A | 11/2009 |
| JP | 2013-511266 A | 4/2013 |
| WO | WO 2007/130738 | 11/2007 |
| WO | WO 2010/050413 A1 | 5/2010 |
| WO | WO 2011/061032 A2 | 5/2011 |
| WO | WO 2013/129667 A1 | 9/2013 |

OTHER PUBLICATIONS

Daverey, "Production, Characterization, and Properties of Sophorolipids from the Yeast *Candida bombicola* using a Low-cost Fermentative Medium" Appl Biochem Biotechnol (2009) vol. 158 pp. 663-674.*

Zhou et al., "Supramolecular Assemblies of a Naturally Derived Sophorolipid" Langmuir (2004) vol. 20 pp. 7926-7932.*

Ma et al., "Effects of nitrogen sources on production and composition of sophorolipids by *Wickerhamiella domercqiae* var. sophorolipid CGMCC 1576" Appl. Microbiol. Biotechnol. (2011) vol. 91 pp. 1623-1632.*

Tulloch et al., "Effects of nitrogen sources on production and composition of sophorolipids by *Wickerhamiella domercqiae* var. sophorolipid CGMCC 1576".*

T. Gu and Y. Zheng, "A Study of Scale-Up of Reversed-Phase Liquid Chromatography." Separation and Purification Technology, 15, 41-58 (1999).*

Shah et al., "Utilization of Restaurant Waste Oil as a Precursor for Sophorolipid Production" Biotechnology Progress vol. 23 pp. 512-515 (Year: 2007).*

(Continued)

*Primary Examiner* — Eric Olson
(74) *Attorney, Agent, or Firm* — Wolf, Greenfield & Sacks, P.C.

(57) ABSTRACT

The present invention provides a high-purity acid-form sophorolipid (SL)-containing composition characterized by substantially not containing acetic acid. The high-purity acid-form SL-containing composition can be produced, for example, by the following method:
(i) adjusting the pH of a partially purified acid-form SL-containing composition to an acidic range; and
(ii-a) subjecting an acidified partially purified acid-form SL-containing composition obtained in step (i) to chromatography to acquire a fraction containing an acid-form SL, or
(ii-b) leaving the acidified partially purified acid-form SL-containing composition obtained in step (i) to stand under a low-temperature condition to acquire a resulting gelled object.

6 Claims, 2 Drawing Sheets

(56) References Cited

OTHER PUBLICATIONS

PCT/JP2014/070788, Nov. 11, 2014, International Search Report and Written Opinion.
PCT/JP2014/073356, Dec. 2, 2014, International Search Report and Written Opinion.
Asmer et al., Microbial production, structure elucidation and bioconversion of sophorose lipids. J American Oil Chem Soc. Sep. 1988;65(9):1460-6.
Brakemeier et al., *Candida bombicola*: production of novel alkyl glycosides based on glucose/2-dodecanol. Appl Microbiol Biotechnol. 1998;50:161-6.
Cavalero et al., The effect of medium composition on the structure and physical state of sophorolipids produced by *Candida bombicola* ATCC 22214. J Biotech. 2003;103:31-41.
Deshpande et al., Evaluation of sophorolipid biosurfactant production by *Candida bombicola* using animal fat. Bioresource Tech. 1995;54(2):143-150.
Hommel, Formation and physiological role of biosurfactants produced by hydrocarbon-utilizing microorganisms. Biosurfactants in hydrocarbon utilization. Biodegradation. 1990;1(2-3):107-19. Review.
Tulloch et al., A new hydroxy fatty acid sophoroside from *Candida bogoriensis*. Can J Chem. Feb. 1, 1968;46(3):345-8.
Zhou et al., Production of sophorose lipids by Torulopsis bombicola from safflower oil and glucose. J American Oil Chem Soc. Jan. 1992;69(1):89-91.
Davila et al., Kinetics and balance of a fermentation free from product inhibition: sophorose lipid production by Candida bombicola. Appl Microbil Biotechnol. 1992;38:6-11.
Ashby et al., Property control of sophorolipids: influence of fatty acid substrate and blending Biotechnol Lett. Jun. 2008;30(6):1093-100. doi: 10-1007/s10529-008-9653-1. EPub Feb. 9, 2008.
Cooper et al., Production of a Biosurfactant from Torulopsis bombicola. Appl Environ Microbiol. Jan. 1984 ;47(1):173-6.
Davila et al., Identification and determination of individual sophorolipids in fermentation products by gradient elution high-performance liquid chromatography with evaporative light-scattering detection. J Chromatogr. Oct. 1, 1993;648(1):139-49.
Gorin et al., Hydroxy fatty acid glycosides of sophorose from torulopsis magnoliae. Can J Chem. 1961;39:846-855.
Hirata et al., Natural synergism of acid and lactone type mixed sophorolipids in interfacial activities and cytotoxicities. J Oleo Sci. 2009;58(11):565-72.
Nuñez et al., LC/MS analysis and lipase modification of the sophorolipids produced by Rhodotorula bogoriensis. Biotechnol Lett. Jul. 2004;26(13):1087-93.
Hirata et al., Natural synergism of acid and lactone type mixed sophorolipids in interfacial activities and cytotoxicities. Journal of Oleo Science, 2009, vol. 58, No. 9, pp. 565-572.
Van Bogaert et al. Microbial production and application of sophorolipids. Appl Microbiol Biotechnol. Aug. 2007;76(1):23-34. Epub May 3, 2007.
[No Author Listed] Altern. Animal Test. Experiment, Guideline Draft. Dec. 1998;5(Supplement):1-3.
Okamoto, Recent developments of Draize eye test alternative in Japan. Fragrance Journal 2005-2;67-71.
Saerens et al., One-step production of unacetylated sophorolipids by an acetyltransferase negative Candida bombicola. Biotechnol Bioeng. Dec. 2011;108(12):2923-31. doi:10.1002/bit.23248. Epub Jul. 12, 2011.
Shah et al., Sophorolipids, microbial glycolipids with anti-human immunodeficiency virus and sperm-immobilizing activities. Antimicrob Agents Chemother. Oct. 2005;49(10):4093-100.
U.S. Appl. No. 14/911,174, filed Feb. 9, 2016, Araki et al.
U.S. Appl. No. 15/061,330, filed Mar. 4, 2016, Ito et al.
Rau et al., Sophorolipids: a source for novel compounds. Industrial Crops Products. Mar. 2001;13(2):85-92.
EP 14843085.3, dated Feb. 23, 2017, Extended European Search Report.
Daniel et al., Sophorolipid Production with High Yields on Whey Concentrate and Rapeseed Oil without Consumption of Lactose. Biotech Lett. Aug. 1998;20(8):805-807.
Examination Report for EP Application No. 148349558 dated Jul. 21, 2017.

\* cited by examiner

HIGH-PURITY ACID-FORM SOPHOROLIPID (SL) CONTAINING COMPOSITION AND PROCESS FOR PREPARING SAME

This application is a national stage filing under 35 U.S.C. § 371 of International Application No. PCT/JP2013/055740, filed Mar. 1, 2013, which claims the benefit of Japanese Patent Application No. JP 2012-047409, filed Mar. 2, 2012, the entire contents of each of which are incorporated by reference herein.

TECHNICAL FIELD

The present invention relates to a high-purity acid-form sophorolipid-containing composition and a method for producing the same.

BACKGROUND ART

Biosurfactants (hereinafter, also referred to as BS), which are surfactants derived from living organisms, have high biodegradability and safety, and are expected to be used industrially as next-generation surfactants.

Sophorolipid, which is known as a glycolipid type BS, is a fermentation product obtained from fermentation by yeast. Sophorolipid can be easily produced by, for example, inoculating yeast on a liquid medium containing carbon sources, such as vegetable oil and fat, and sugars such as glucose, and stirring the medium while aerating the medium at a mild temperature and under pressure. Compared to other BSs, sophorolipid can be obtained with high productivity (e.g., about 100 g/L), and has been industrially used (Non-Patent Literature 1).

However, in the fermentation generation process of sophorolipid, since fermentation by-products (various organic acids and salts thereof, pigments, etc.) are also simultaneously produced, partially purified or partially extracted sophorolipid obtained after the end of fermentation emits specific odors. Therefore, there have been limits and many problems that needed to be solved in order to apply sophorolipid to drugs, quasi drugs, food products, and cosmetics.

For example, quasi drugs and cosmetics used on the body include rinse-off type products, such as shampoos (body shampoo, hair shampoo) and hair rinses, which are applied to the skin and then washed away, and leave-on type products, such as face lotions and milky lotions, which are applied and maintained on the skin. Since the pH of the skin is weakly acidic, weakly acidic products of both types minimally affect the skin, and market needs for such products are high. However, since hitherto known sophorolipids contain a large amount of various organic acids derived from fermentation, weakly acidic cosmetics and the like having such sophorolipids blended therein emit characteristic odors, and are not fit for use. These odors originate from lower fatty acids, such as acetic acid, butyric acid, and isovaleric acid, and there are techniques to reduce the odors through masking methods, etc. However, since the olfactory threshold (the minimum concentration of odor that can be sensed) for lower fatty acids is extremely low, and lower fatty acids have a high skin persistency due to having low volatility, an unpleasant acid odor remains over a long period of time.

In recent years, coenzyme Q10 and hyaluronic acid have been widely used in food products and cosmetics, and many studies have been conducted thereon since they have various bioactivities. At present, they are blended in many products to utilize their function. On the other hand, although sophorolipid, which is also a natural product, has been found to have unique functions, such as controlling emulsification power and percutaneous absorption of active ingredients (Patent Literature 1), actual usage examples thereof in external use compositions, such as cosmetics, are nonexistent.

The reason why there has not been much progress in the industrial use of sophorolipid, even though it is a material derived from living organisms, has high capability, and has high biodegradability and safety, is no other than the lack of a deodorization or impurity removing method on an industrial scale.

Generally, a purification process is the most difficult and costly process in producing a fermentation product. The reasons for this include the amount of fermentation products obtained from fermentation being remarkably small, for example, not more than 1 mass % per 100 mass % of liquid obtained at the end of fermentation. Thus, in a situation where a useful substance that has been produced through fermentation is extremely diluted and diffused in a liquid obtained at the end of fermentation, it is necessary to selectively extract or concentrate, etc., the intended useful substance. Sophorolipid, which is the target of the present invention, is no exception even though the productivity thereof is high.

For the purification of sophorolipid, many of the hitherto reported methods involve extraction by adding, to a liquid culture medium, an equivalent amount of hexane and ethyl acetate (e.g., Non-Patent Literature 2). However, the sophorolipid obtained from such methods still has characteristic odors. This is because odor components have properties chemically similar to sophorolipid, and are extracted in a manner similar to sophorolipid.

There is also a report of a method for purifying sophorolipid as a white substance (Non-Patent Literature 3). Here, a liquid culture medium itself is lyophilized, ethyl acetate is added to the dried object, the mixture is stirred at 30° C. for 2 days, ethyl acetate is distilled off, and a crystal is formed using hexane. However, in this method, since it is necessary to add a flammable organic solvent and leave it over several days, it is difficult to put the method to practical use. In addition, the sophorolipid obtained from this method still has slight odors.

Furthermore, with the method described above, it is necessary to recover or remove the organic solvent from a collected liquid. Therefore, energy and special equipment are required for treating waste liquid containing the organic solvent, resulting in an increase in cost. In addition, such usage of organic solvents requires strict management thereof from a standpoint of environmental impact and adverse health effects. Furthermore, when there is a possibility of an organic solvent remaining in the obtained sophorolipid, it becomes undesirable for application to food products and cosmetics. Thus, hitherto known methods of extraction, isolation, and purification are proposed merely from a standpoint of basic research, and industrial application is not taken into consideration.

From the standpoint of industrial application, purification has to be a process that is cheap and safe. When it is a widely used chemical product, the cost aspect becomes particularly important. Furthermore, at present, in addition to the biodegradability of a used product, it is important to establish a safer manufacturing process including the raw materials from a standpoint of LCA (Life Cycle Assessment). Therefore, for a sophorolipid that is derived from living organisms and is safe for a living body, it is also preferable to establish a production method without discharging or using hazardous organic solvents.

Therefore, establishment of a method for producing highly pure acid-form sophorolipid stably, cheaply, and with a high yield without using hazardous organic solvents is expected to dramatically advance the industrial application of sophorolipid as a new material that is derived from living organisms, is safe, and has excellent biodegradability.

CITATION LIST

Patent Literature

PTL 1: JP2009-062288A
PTL 2: JP2002-045195A
PTL 3: JP2003-009896A
PTL 4: JP2008-247845A

Non-Patent Literature

NPL 1: Gorin, Can. J Chem., 39, 846 (1961)
NPL 2: D. G. Cooper and D. A. Paddock, Appl. Environ. Microbiol., 47, 173-176 (1984)
NPL 3: R. D. Ashby, D. K. Y. Solaiman and T. A. Foglia, Biotechnol. Lett., 30, 1093-1100, 2008
NPL 4: Hirata, Y., Ryu, M., Igarashi, K., Nagatsuka, A., Furuta, T., Kanaya, S., and Sugiura, M. (2009) Natural synergism of acid and lactone type mixed sophorolipids in interfacial activities and cytotoxicities. J. Oleo. Sci., 58, 565-572

SUMMARY OF INVENTION

Technical Problem

An object of the present invention is to provide a high-purity acid-form sophorolipid-containing composition having removed therefrom fermentation by-products generated in a fermentation generation process, in particular, odor components that become a cause of a smell (particularly acetic acid which becomes a cause of an irritative odor). Furthermore, an object of the present invention is to provide a method for producing the high-purity acid-form sophorolipid-containing composition.

Solution to Problem

The present inventors have conducted thorough research in order to solve the above described problem, and, as a result, surprisingly found that by adjusting the pH of a partially purified acid-form sophorolipid-containing composition obtained from a fermentation generation process to an acidic range, and then subjecting the composition to chromatography or gelling the composition under a low-temperature condition, it becomes possible to significantly remove fermentation by-products, particularly the acetic acid that becomes a cause of an irritative odor, and to acquire a desired high-purity acid-form sophorolipid-containing composition. They have further conducted research and completed the present invention.

Thus, the present invention relates to an acid-form sophorolipid-containing composition that contains a highly pure acid-form sophorolipid, and a method for the production thereof. Hereinafter, in the present specification, for the purpose of distinguishing this composition from a hitherto known acid-form sophorolipid-containing composition, the acid-form sophorolipid-containing composition of the present invention is also referred to as a "high-purity acid-form sophorolipid-containing composition" or a "high-purity acid-form SL-containing composition" by abbreviating "sophorolipid" to "SL."

(I) High-Purity Acid-Form Sophorolipid-Containing Composition (I-1) A high-purity acid-form SL-containing composition (1), the composition substantially not containing acetic acid.

(I-2) The high-purity acid-form SL-containing composition according to (I-1), the composition having physical properties of the following (2) and (3):
  (2) ignition residue: 0 to 30%; and
  (3) ester value: 0 to 20 mg KOH/g.

(I-3) The high-purity acid-form SL-containing composition according to (I-2), the composition having at least one physical property among the following (4) to (6):
  (4) evaporation residue: 1 to 100%;
  (5) drying loss: 0 to 99%; and
  (6) ethanol soluble matter: 1 to 100%.

(I-4) The high-purity acid-form SL-containing composition according to any one of (I-1) to (I-3), the composition having, in an infrared absorption spectrum, infrared-ray absorption bands at least at wavenumbers of around 1024 $cm^{-1}$, around 1706 $cm^{-1}$, around 2854 $cm^{-1}$, around 2924 $cm^{-1}$, and around 3000 to 3500 $cm^{-1}$.

(I-5) The high-purity acid-form SL-containing composition according to any one of (I-1) to (I-4), the composition having a solid form.

(I-6) The high-purity acid-form SL-containing composition according to (I-5), wherein the solid form is a powder or granule.

(II) Use Application of High-Purity Acid-Form Sophorolipid-Containing Composition (II-1) A perfumery or cosmetic, food or beverage, quasi drug, or drug, comprising the high-purity acid-form SL-containing composition according to any one of (I-1) to (I-6).

(II-2) The perfumery or cosmetic, food or beverage, quasi drug, or drug according to (II-1), wherein the food or beverage is a health supplement, a health functional food product, food for specified health use, or a supplement.

(II-3) The perfumery or cosmetic, food or beverage, quasi drug, or drug according to (II-1), wherein the perfumery or cosmetic, quasi drug, or drug is applied to a body through rubbing, spraying, or another method similar to those.

(III) Method for Producing High-Purity Acid-Form Sophorolipid-Containing Composition (III-1) A method for producing the high-purity acid-form SL-containing composition according to any one of (I-1) to (I-6), the method comprising the following step (i), and step (ii-a) or (ii-b):
  (i) adjusting the pH of a partially purified acid-form SL-containing composition to an acidic range;
  (ii-a) subjecting an acidified partially purified acid-form SL-containing composition obtained in step (i) to chromatography to acquire a fraction containing an acid-form SL; and
  (ii-b) leaving the acidified partially purified acid-form SL-containing composition obtained in step (i) under a low-temperature condition to acquire a resulting gelled object.

(III-2) The method according to (III-1), wherein the partially purified acid-form SL-containing composition is an acid-form SL-containing composition obtained through alkali hydrolysis of a liquid culture of a sophorolipid producing yeast or a processed product of the liquid culture.

(III-3) The method for producing the high-purity acid-form SL-containing composition according to (III-1) or (III-2), the method comprising the steps of (i) and (ii-a), wherein the acidic range is lower than pH 6.

(III-4) The method for producing the high-purity acid-form SL-containing composition according to any one of (III-1) to (III-3), the method comprising the steps of (i) and (ii-a), wherein the chromatography is reverse phase column chromatography.

(III-5) The method according to (III-4), wherein the reverse phase column chromatography is column chromatography using ODS resin as a column filler.

(III-6) The method according to (III-5), wherein the reverse phase column chromatography is chromatography using an aqueous ethanol solution as an eluent, and the method comprises a step of, after loading the acidified partially purified acid-form SL-containing composition obtained in step (i) into a column filler (stationary phase) and washing the column filler with an aqueous ethanol solution whose ethanol concentration is approximately not lower than 10 vol % but lower than 60 vol %, eluting and acquiring a fraction containing an acid-form SL by supplying an aqueous ethanol solution whose ethanol concentration is approximately 70 to 90 vol %.

(III-7) The method for producing the high-purity acid-form SL-containing composition according to (III-1) or (III-2), the method comprising the steps of (i) and (ii-b), wherein the acidic range is not higher than pH 4 and preferably pH 1 to 4, and the low-temperature condition is not higher than 15° C. and preferably not higher than 10° C.

(III-8) The method for producing the high-purity acid-form SL-containing composition according to (III-1), (III-2), or (III-7), the method comprising the steps of (i) and (ii-b), and further comprising a step of washing the gelled object obtained in step (ii-b) with cold water.

(III-9) The method according to any one of (III-1) to (III-8), the method further comprising the following steps:

(iii) distilling a liquid high-purity acid-form SL-containing composition obtained via step (i) and step (ii-a) or (ii-b), and (iv) precipitating an acid-form SL from a residual liquid obtained from the distillation.

(III-10) The method according to (III-9), wherein step (iv) is a step of spray-drying.

(III-11) The method according to any one of (III-1) to (III-8), the method further comprising the following steps:

(v) solidifying, through cooling, the high-purity acid-form SL-containing composition obtained via step (i) and step (ii-a) or (ii-b); and (vi) drying the cooling-solidified object.

(III-12) The method according to (III-11), wherein the steps of (v) and (vi) are lyophilization steps.

Advantageous Effects of Invention

The production method of the present invention is industrially advantageous, since a highly pure and chemically stable acid-form SL can be isolated and purified safely with less energy at a high recovery rate. Furthermore, the high-purity acid-form SL-containing composition of the present invention can be easily blended in various formulations, such as cosmetics, because of not having undesirable odors, since impurities, such as fermentation by-products generated in the fermentation generation process, particularly odor components such as acetic acid, are removed from the composition. The composition is particularly suitable for quasi drugs and cosmetics for skin, etc., in which a weakly acidic composition is preferred.

DESCRIPTION OF EMBODIMENTS (I) Sophorolipid

Figure 1:
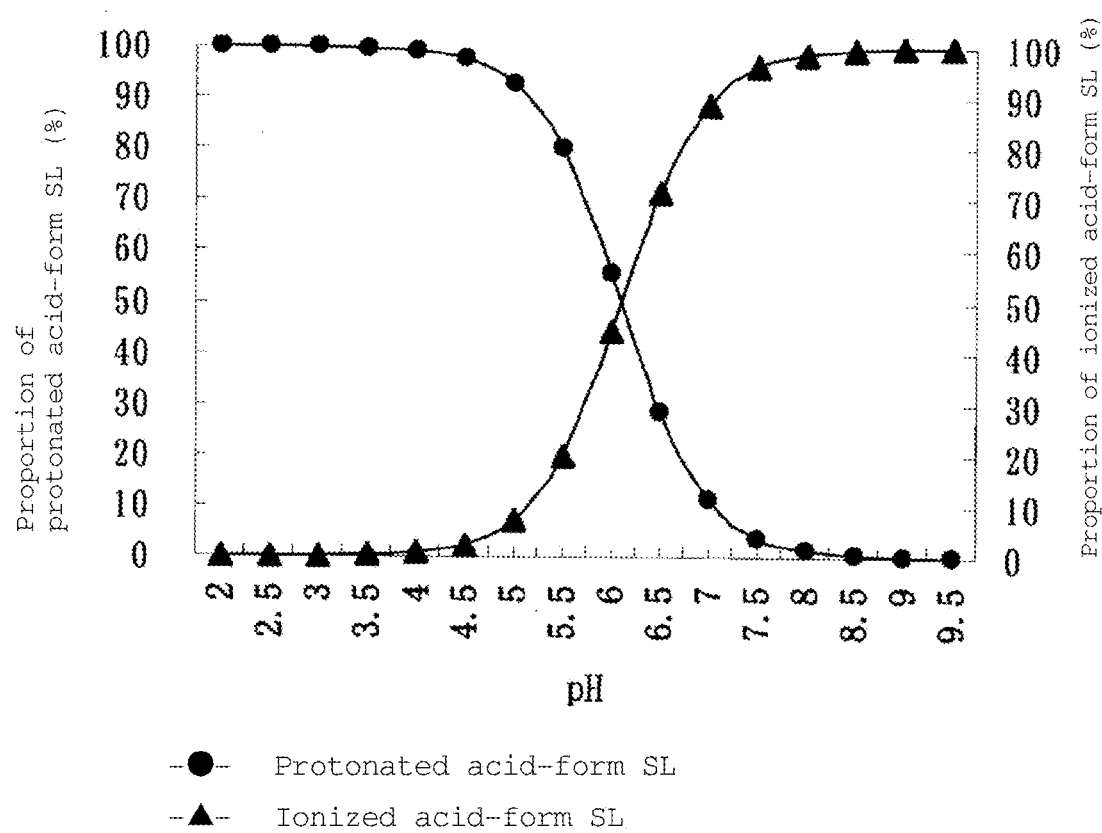
FIG. 1 shows the behavior of a high-purity acid-form SL-containing composition of the present invention in a range of pH 2 to 9.5 when its pKa is 6.1.

Sophorolipid (SL) is a glycolipid consisting of a hydroxyl fatty acid, and sophorose or a sophorose whose hydroxyl group is partially acetylated. It should be noted that sophorose is a sugar consisting of two glucose molecules bound through a β1→2 bond. A hydroxyl fatty acid is a fatty acid having a hydroxyl group. Furthermore, SL is classified largely into an acid form (General Formula (1)) or a lactone form (General Formula (2)) in which the carboxyl group of the hydroxy fatty acid is free or bound to the sophorose within the molecule, respectively. SL obtained from a certain species of yeast (SL-producing yeast) through fermentation is ordinarily a mixture of the SL shown in the following General Formula (1) and the SL shown in the following General Formula (2), and is obtained as a collection of 30 or more types of structural homologs having different fatty acid chain lengths ($R^3$), and having an acetylation or protonation at the 6'-position ($R^2$) and the 6''-position ($R^1$) of the sophorose.

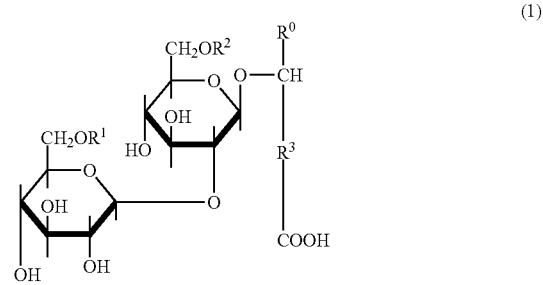

(1)

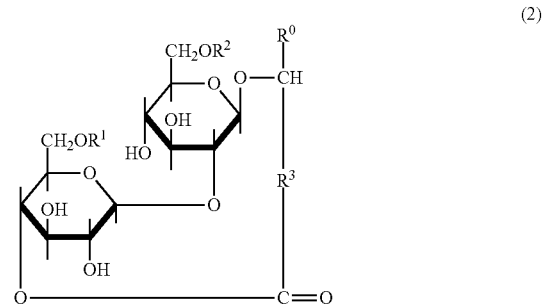

(2)

In General Formula (1) or (2), $R^0$ is either a hydrogen atom or a methyl group. $R^1$ and $R^2$ are each independently a hydrogen atom or an acetyl group. $R^3$ is a saturated aliphatic hydrocarbon chain or an unsaturated aliphatic hydrocarbon chain having at least one double bond, and may have one or more substituent groups. The substituent group is not particularly limited as long as the advantageous effect of the present invention is not hindered, and examples thereof include halogen atoms, hydroxyl, lower ($C_{1-6}$) alkyl groups, halo lower ($C_{1-6}$) alkyl groups, hydroxy lower ($C_{1-6}$) alkyl groups, halo lower ($C_{1-6}$) alkoxy groups, and the like. Furthermore, $R^3$ typically has 11 to 20 carbon atoms, preferably 13 to 17 carbon atoms, and more preferably 14 to 16 carbon atoms.

As described above, in a liquid culture obtained through fermentation by an SL-producing yeast, SL ordinarily exists as a mixture of the acid-form SL (the SL shown in General Formula (1)) and the lactone-form SL (the SL shown in General Formula (2)). Among those, since the lactone-form SL is a nonionic oily substance and is extremely insoluble in water by itself, it is undesirable to have the lactone-form SL in a high proportion because it causes a sophorolipid mixture to become water insoluble as a whole (Non-Patent Literature 4). On the other hand, it is preferable to have the acid-form SL in a high proportion since it is chemically stable as compared to the lactone-form SL.

Generally, an acid-form sophorolipid-containing composition (acid-form SL-containing composition) refers to a composition containing, relative to 100 mass % of sophorolipid contained in the composition, 78 mass % or more of the acid-form SL shown in General Formula (1), and the remaining less than 22 mass % of the lactone-form SL shown in General Formula (2).

Hereinafter, in the present specification, regarding a composition (including a liquid culture and a processed product thereof) containing SL produced through fermentation by an SL-producing yeast; relative to 100 mass % of SL contained in the composition, a composition whose content proportion of the acid-form SL is 78 mass % or more is collectively referred to as "acid-form sophorolipid-containing composition (acid-form SL-containing composition)," and a composition whose content proportion of the acid-form SL is less than 45 mass % and whose content proportion of the lactone-form SL is the remaining 55 mass % or more is referred to as "lactone-form/acid-form sophorolipid-containing composition (lactone-form/acid-form SL-containing composition)."

Furthermore, in the present invention, the above described acid-form SL-containing composition can be classified in many ways, such as partially purified acid-form SL-containing composition, acidified partially purified acid-form SL-containing composition, and high-purity acid-form SL-containing composition, depending on the degree of purification (purity) of the acid-form SL, the contained amount of non-volatile components, the content proportion of the acid-form SL, liquid properties, etc.

It should be noted that the high-purity acid-form SL-containing composition described here is the acid-form SL-containing composition of the present invention characterized by substantially not containing acetic acid (described later), and other acid-form SL-containing compositions, i.e., acid-form SL-containing compositions that contain acetic acid, are classified as "partially purified acid-form SL-containing compositions" with varying SL content proportions and acid-form SL purity.

(II) High-Purity Acid-Form Sophorolipid-Containing Composition

The high-purity acid-form SL-containing composition, which is the target of the present invention, is different from, at least in terms of odor, hitherto known acid-form SL-containing compositions (including the above described lactone-form/acid-form SL-containing composition and partially purified acid-form SL-containing composition), and has the following feature:

(1) substantially not containing acetic acid.

Here, "substantially not containing acetic acid" refers to the contained amount of acetic acid being lower than the detection limit when measured with, for example, an ordinary analysis method, such as gas chromatography. Thus, even when acetic acid is contained in an ultra-minute amount, if it is not measurable with an ordinary analysis method (lower than the detection limit), the acid-form SL-containing composition may be regarded as substantially not containing acetic acid.

Here, examples of an "ordinary analysis method" include: a method by neutralization titration using an alkaline solution; methods of detecting an acetic acid peak using high performance liquid chromatography (HPLC) or gas chromatography; a method using a gas detector tube system manufactured by Gastec Corp.; and an enzymatic method using an F-kit for acetic acid manufactured by Roche Diagnostics.

More specifically, examples thereof include an analysis method using "headspace gas chromatography with a hydrogen flame ionization detector" described in Test Example 1. When 1 g equivalent of an ethanol soluble matter of the target acid-form SL-containing composition is analyzed at least in accordance with a method described in Test Example 1, if the value is lower than the detection limit, i.e., lower than a "5 μg/1 ml syringe" and if acetic acid cannot be detected, the acid-form SL-containing composition can be considered as the high-purity acid-form SL-containing composition of the present invention.

It should be noted that, in Test Example 1, a "reference production example product 1" is a lactone-form/acid-form SL-containing composition used as a raw material for producing the high-purity acid-form SL-containing composition of the present invention, and a "comparative example product 2" is a partially purified acid-form SL-containing composition obtained through purification by hexane extraction and alkali hydrolysis based on the description in Non-Patent Literature 2 (hereinafter, these are collectively referred to as "conventional products" for convenience). As shown in Test Example 1, these conventional products have a strong irritative odor since they contain acetic acid in a concentration of 300 μg/ml or more, but the high-purity acid-form SL-containing composition of the present invention substantially does not contain acetic acid, and clearly differs from the conventional products in terms of not having an irritative odor caused by acetic acid.

Furthermore, in the high-purity acid-form SL-containing composition of the present invention, the contained amount of other odor components is also significantly reduced when compared to a conventional product as shown in Test Example 1. According to the analysis method using "headspace gas chromatography with a hydrogen flame ionization detector" adopted in Test Example 1, the total odor concentration detected in 1 g equivalent of ethanol soluble matter of the acid-form SL-containing composition is not higher than 10,000 μg/ml, preferably not higher than 8,000 μg/ml, more preferably not higher than 5,000 μg/ml, further preferably not higher than 3,000 μg/ml, even further preferably not higher than 2,000 μg/ml, and particularly preferably not higher than 1,000 μg/ml or not higher than 500 μg/ml.

Therefore, since the high-purity acid-form SL-containing composition of the present invention does not have the irritative odor caused by acetic acid, and the odor caused by other odor components is also markedly faint, the high-purity acid-form SL-containing composition is odorless or almost odorless.

Here, other odor components include odor components generated in the SL generation process (fermentation generation process) during fermentation by the SL-producing yeast, and lower fatty acids other than acetic acid are illustrated as one type thereof. Here, lower fatty acid (including acetic acid) is a collective term of monocarboxylic acids having a chain structure represented by RCOOH (R is a hydrocarbon having 1 to 5 carbon atoms). Although such a lower fatty acid is soluble in water, it has an irritative odor and sourness, and is an odor component that is generally avoided. For example, valeric acid represented by $CH_3(CH_2)_3COOH$ has an odor that is like a sweaty sock, and is a compound that is regulated by the Offensive Odor Control Law since it has an extremely low olfactory threshold.

Since such lower fatty acids other than acetic acid are soluble in water in a manner similar to acetic acid, they are removed, similar to acetic acid, when isolating and purifying the acid-form SL from the liquid culture of the SL-producing yeast during the production of the high-purity acid-form SL-containing composition of the present invention. Therefore, when the acetic acid content is measured using headspace gas chromatography with a hydrogen flame ionization detector, if the acetic acid content is less than the detection limit, it can be considered that the lower fatty acids other than acetic acid are also removed, similar to acetic acid, or at least the amount contained is reduced. Therefore, in the present invention, "substantially not containing acetic acid" may also be referred to as "substantially not containing lower fatty acids (including acetic acid)." Thus, although the high-purity acid-form SL-containing composition of the present invention has a feature of substantially not containing acetic acid, the composition preferably also has a feature of substantially not containing both acetic acid and lower fatty acids other than acetic acid, and does not have irritative odors caused by acetic acid and lower fatty acids other than acetic acid.

Furthermore, the high-purity acid-form SL-containing composition, which is the target of the present invention, has the following physical properties of (2) and (3):

(2) ignition residue: 0 to 30%; and
(3) ester value: 0 to 20 mg KOH/g.

Here, "ignition residue (%)" is a ratio of inorganic compounds (sulfate equivalent) contained in a sample as described in Test Example 2, and the "ignition residue" allows an understanding of the contained amount, as an amount of sulfate, of inorganic compounds contained as impurities in the sample i.e., the acid-form SL-containing composition in the present invention. The "ignition residue (%)" can be measured in accordance with the First Method in the Japanese Standards of Quasi-drug Ingredients 2006 (Japan) or JIS K0067-1992. Details thereof are as described in Test Example 2. The ignition residue (%) of the high-purity acid-form SL-containing composition of the present invention is 0 to 30%, preferably 0 to 20%, more preferably 0 to 10%, and particularly preferably 0%.

Furthermore, "ester value (mg KOH/g)" is the amount of potassium hydroxide expressed in milligrams required for complete saponification of esters contained in 1 g of the sample as described in Test Example 2, and the "ester value" allows an understanding of the ratio of ester bonds in lactone rings and acetyl groups in the sample i.e., the acid-form SL-containing composition in the present invention. The "ester value (mg KOH/g)" can be measured in accordance with the JOCS Standard Methods for the Analysis of Fats, Oils and Related Materials (2.3.3-1996) defined by the Japan Oil Chemists' Society (Japan). Details thereof are as described in Test Example 2. The ester value (mg KOH/g) of the high-purity acid-form SL-containing composition of the present invention is 0 to 20 mg KOH/g, preferably 0 to 18 mg KOH/g, more preferably 0 to 9 mg KOH/g, and particularly preferably 0 mg KOH/g.

It should be noted that there is a correlation between the ester value (mg KOH/g) of the high-purity acid-form SL-containing composition of the present invention and the proportion of the lactone-form SL in 100 mass % of SL contained in the high-purity acid-form SL-containing composition, and the relationship thereof is that the proportion of the lactone-form SL is high when the ester value (mg KOH/g) is high, whereas the proportion of the lactone-form SL is low when the ester value (mg KOH/g) is low.

More specifically, when the molecular weight of the acid-form SL is 621 (when the fatty acid bound to sophorose through a glycosidic bond is oleic acid), when the molecular weight of the lactone-form SL is 603 (when the carboxyl group of the acid-form SL is bound to sophorose in the molecule through an ester bond), and when the molecular weight of potassium hydroxide is 56.1, the lactone-form SL and potassium hydroxide undergo alkaline degradation as shown in the formula below.

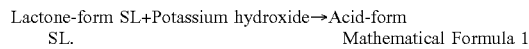

Lactone-form SL+Potassium hydroxide→Acid-form SL.  Mathematical Formula 1

Thus, when the target of alkaline degradation is the ester bond of the lactone-form SL, if the ester value is low, the proportion of the lactone-form SL contained in the acid-form SL-containing composition becomes low.

Therefore, the proportion of the acid-form SL contained in 100 mass % of the high-purity acid-form SL-containing composition of the present invention is, in solid equivalent, 78 to 100 mass %, preferably 80 to 100 mass %, more preferably 90 to 100 mass %, and particularly preferably 100 mass %.

Furthermore, in addition to the above (1), (2), and (3); the high-purity acid-form SL-containing composition which is the target of the present invention has at least one physical property among the following (4) to (6):

(4) evaporation residue: 1 to 100%;
(5) drying loss: 0 to 99%; and
(6) ethanol soluble matter: 1 to 100%.

Here, "evaporation residue (%)" represents, in mass percentage (mass %), the residue obtained through evaporation of the sample as described in Test Example 2, and the evaporation residue allows an understanding of the contained amount of coexisting substances, particularly coexisting substances having a high boiling point in the sample, i.e., the acid-form SL-containing composition in the present invention. The evaporation residue (%) can be measured in accordance with The Second Method in JIS K0067-1992. Details thereof are as described in Test Example 2. The evaporation residue (%) of the high-purity acid-form SL-containing composition of the present invention is sufficient when it is in a range of 1 to 100%, preferably 5 to 100%, and more preferably 10 to 100%; however, the evaporation residue is further preferably 60 to 100%, even further preferably 70 to 100%, particularly preferably 80 to 100%, and further particularly preferably 90 to 100%.

Furthermore, "drying loss (%)" represents the loss in mass percentage (mass %) of the sample when it is dried as described in Test Example 2, and the drying loss allows an understanding of the contained amount of water and other volatile substances (low-boiling-point compounds) in the sample i.e., the acid-form SL-containing composition in the present invention. The drying loss (%) can be measured in accordance with the First Method in JIS K0067-1992. Details thereof are as described in Test Example 2. The drying loss (%) of the high-purity acid-form SL-containing composition of the present invention is sufficient when it is in a range of 0 to 99%, preferably 0 to 95%, and more preferably 0 to 90%; however, the drying loss is further preferably 0 to 30%, even further preferably 0 to 20%, particularly preferably 0 to 20%, and further particularly preferably 0 to 10%.

Furthermore, "ethanol soluble matter (%)" represents the contained amount (mass %) of substances that are soluble in ethanol and are contained in the sample as described in Test Example 2, and the ethanol soluble matter allows an understanding of the contained amount of ethanol soluble polar substances such as, for example, surfactants, mixed in the sample. The ethanol soluble matter (%) can be measured in accordance with JIS K3362-2008. Details thereof are as described in Test Example 2. The ethanol soluble matter (%) of the high-purity acid-form SL-containing composition of the present invention is sufficient when it is in a range of 1 to 100%, preferably 5 to 100%, and more preferably 10 to 100%; however, the ethanol soluble matter is further preferably 85 to 100%, even further preferably 90 to 100%, in particularly preferably 95 to 100%, and further particularly preferably 98 to 100%. The ethanol soluble matter (%) represents the content proportion (mass %) of the acid-form SL and lactone-form SL, when the target sample or acid-form SL-containing composition in the present invention is defined as 100 mass %.

More preferably, the high-purity acid-form SL-containing composition of the present invention has, in an infrared absorption spectrum, infrared-ray absorption bands (absorption peaks) at least at wavenumbers of around 1024 cm$^{-1}$, around 1706 cm$^{-1}$, around 2854 cm$^{-1}$, around 2924 cm$^{-1}$, and around 3000 to 3500 cm$^{-1}$. As shown in Test Example 2, in particular, the peak around wavelength 1706 cm$^{-1}$ is not observed in conventional products, and is a peak observed specifically in the high-purity acid-form SL-containing composition of the present invention.

As long as the above described properties exist, the high-purity acid-form SL-containing composition of the present invention further includes a composition in which approximately 85% or more of peak total area obtained from an HPLC analysis is the acid-form SL. It should be noted that the HPLC analysis conditions are as described in Examples (Table 1), and the peak total area obtained from the HPLC analysis represents the total amount of components that are not volatile under a nitrogen gas condition at 40° C. in the high-purity acid-form SL-containing composition of the present invention. Furthermore, when measurement is conducted under these conditions, a peak detected at a retention time of 8 to 25 minutes represents the acid-form SL, a peak detected at a retention time of 25 to 45 minutes represents the lactone-form SL, and peaks detected at a retention time of 45 to 55 minutes represent higher fatty acids. Here, the proportion of the acid-form SL contained in the high-purity acid-form SL-containing composition is calculated from the ratio of the peak area of the acid-form SL with respect to the total value of the peak area of the acid-form SL, the peak area of the lactone-form SL, and the peak area of higher fatty acids. It should be noted that the difference between the above described "lactone-form/acid-form SL-containing composition" and "acid-form SL-containing composition" can be determined by subjecting, to HPLC, a composition containing SL which is the target with the above described conditions, and calculating the content proportion of the acid-form SL relative to the total amount of SL, defined as 100 mass %, obtained from the total value (total area value) of the peak area of the acid-form SL and the peak area of the lactone-form SL.

The proportion of the acid-form SL in the high-purity acid-form SL-containing composition is, as described above, not lower than approximately 85%, preferably not lower than approximately 90%, and more preferably not lower than approximately 95%. It should be noted that the remainder of approximately 15% or lower, preferably approximately 10% or lower, and more preferably approximately 5% or lower includes the lactone-form SL and higher fatty acids.

Furthermore, in the acid-form SL contained in the high-purity acid-form SL-containing composition of the present invention, the fatty acid bound to sophorose through a glycosidic bond is not particularly limited as long as the advantageous effect of the present invention is not hindered; and examples thereof include saturated or unsaturated fatty acids having 10 to 22 carbon atoms, such as oleic acid, palmitic acid, stearic acid, and linolic acid. With regard to these fatty acids, a single type may be used by itself, or a combination of any two or more fatty acids may be used. The composition proportion is not limited. Oleic acid is preferably contained in a proportion of not lower than approximately 85%, and preferably approximately 85 to 93%; and a proportion of approximately 2 to 5% of palmitic acid, approximately 1 to 3% of stearic acid, and/or approximately 4 to 7% of linolic acid is preferable.

The form of the high-purity acid-form SL-containing composition of the present invention is not particularly limited, and may be a liquid form, an emulsion form, or a solid form. A solid form is preferable, and examples of the solid form include a tablet form, a pill form, a powder form, a granule form, and a capsule form. The composition is preferably in a powder form or a granule form, and more preferably in a powder form.

The high-purity acid-form SL-containing composition of the present invention has little contamination of impurities such as fermentation by-products produced in the manufacturing process, and does not have undesirable odors as described above. Therefore, the composition can be suitably used as an additive such as, for example, a surfactant for food or beverages, drugs, quasi drugs, perfumery or cosmetics, and the like whose odor is an important factor in determining its commercial value. It should be noted that, food or beverage as described here includes, other than general food products and beverages, food and beverages that have specific functions and are taken for maintaining health, etc., such as health supplements, health functional food products, food for specified health use, supplements, or the like. In addition, perfumery and cosmetics are used here as concepts including "cosmetics" and "fragrance products" such as scented water, cologne, and perfume. It should be noted that cosmetics are those applied to the body through rubbing, spraying, and other methods (e.g., pasting) similar to those for purposes such as cleaning, beautifying, and increasing the attractiveness of a person's body to change one's physical appearance, or maintaining the health of the skin or hair; and examples of cosmetics include make-up cosmetics (foundation, lipstick, etc.), basic cosmetics (face lotion, milky lotion, etc.), hair care products (hair tonic, hair lotion, hair cream, etc.), and toiletry products (toothpaste, shampoo, hair rinse, soap, facial wash, bath fragrance, etc.).

As described above, since impurities such as fermentation by-products, particularly acetic acid, which becomes a cause of an irritative odor, are significantly removed from the high-purity acid-form SL-containing composition of the present invention, and since the composition has an extremely small amount of other odor components contained therein, the composition is suitably used particularly in quasi drugs (external use compositions), cosmetics, and the like for skin where a weakly acidic composition is preferred. Furthermore, as shown in Example 4 and Test Example 3, since the high-purity acid-form SL composition of the present invention can retain water and the like due to the formation of a mesh-like network under, for example, an acidic low-temperature condition through intermolecular interaction, the composition can be used, for example, as a gelling agent and the like.

(III) Method for Producing the High-Purity Acid-Form Sophorolipid-Containing Composition of the Present Invention The above-described high-purity acid-form SL-containing composition of the present invention can be prepared using a production method having the following step (i), and either step (ii-a) or (ii-b):

(i) adjusting the pH of a partially purified acid-form SL-containing composition to an acidic range;

(ii-a) isolating, by chromatography, an acidified partially purified acid-form SL-containing composition obtained in step (i); and (ii-b) leaving the acidified partially purified acid-form SL-containing composition obtained in step (i) to stand under a low-temperature condition to obtain a gel.

In other words, the high-purity acid-form SL-containing composition of the present invention can be produced by a production method including the steps of (i) and (ii-a) (hereinafter, this is referred to as "production method A"), or a production method including the steps of (i) and (ii-b) (hereinafter, this is referred to as "production method B").

In the following, details of each of the steps in "production method A" and "production method B" will be described.

(III-1) Production Method a (a) Material (Partially Purified Acid-Form Sophorolipid-Containing Composition)

As an aqueous solution containing a partially purified acid-form sophorolipid (hereinafter, also simply referred to as "partially purified acid-form SL-containing composition") used in step (i), a wide range of liquids containing sophorolipid (SL) can be used as long as the advantageous effect of the present invention is not hindered. Preferably, a fraction containing the acid-form SL isolated from a liquid culture obtained from culturing yeast is used. SL is obtained by culturing a microorganism, and is produced by culturing yeast such as, for example, Starmerella (Candida) bombicola, C. apicola, C. petrophilum, Rhodotorula (Candia) bogoriensis, C. batistae, C. gropengiesseri, Wickerhamiella domercqiae, and Yarrowia lipolytica with a method known in the art. In the present invention, these yeasts are referred as "SL-producing yeasts." The yeast may be a strain provided from a deposit institution or a strain obtained from successive subculturing thereof. Here, an SL produced by Rhodotorula (Candia) bogoriensis NRCC9862 is 13-[(2'-O-beta-D-glucopyranosyl-beta-D-glucopyranosyl)oxy]docosanoic acid 6',6"-diacetate, and a glycosidic bond is formed between sophorose and a hydroxyl group at the center of an alkyl group. Although the SL is different from the General Formulae (1) and (2), it is the same from the standpoint of being formed from sophorose and a hydroxyl fatty acid, and is included in the SL which is the target of the present invention.

As an example of the method for culturing yeast to produce SL (SL-producing yeast), a method of culturing by simultaneously providing a high concentration of a sugar and a hydrophobic oily substrate is preferable. The method is not limited thereto, and a wide range of other methods known in the art can be applied as long as the advantageous effect of the present invention is not hindered. The method known in the art may be a method described in JP2002-045195A (Patent Literature 2), etc. More specifically, the method may be a technique of culturing Starmerella (Candida) bombicola as the production yeast using glucose as the sugar, and carbon sources including a fatty acid and vegetable oil as the hydrophobic oily substrate.

The medium composition is not particularly limited, and since it is known that the fatty acid moiety of SL depends on the fatty acid chain length and proportion of the hydrophobic substrate added as a medium component, the fatty acid moiety can be controlled to a certain degree. For example, as the hydrophobic substrate, oleic acid or a lipid containing oleic acid in a high proportion is suitable. Examples thereof include vegetable oils such as palm oil, rice bran oil, rapeseed oil, olive oil, and safflower oil, and animal oils such as lard and beef fat. Furthermore, when a mixed substrate of triglyceride and oleic acid is used as the hydrophobic substrate, it is possible to obtain a sophorolipid containing oleic acid in a high proportion with a high yield in terms of quantity and efficiency. From the standpoint of industrial use, the fermentative production of SL stably and with a high yield in terms of quantity and efficiency is demanded. In this case, a mixture of hydrophilic sugar and hydrophobic fat/oil is preferable as a carbon source. Glucose is frequently used as the hydrophilic substrate.

From the obtained liquid culture, for example, by separating and removing the liquid component by a hitherto known solid-liquid-separation method such as centrifugal separation and decantation, and washing the solid content with water, an SL-containing fraction can be obtained. The SL-containing fraction is a mixture of the lactone-form SL and the acid-form SL, and is classified as a lactone-form/acid-form SL-containing composition since its content proportion of the acid-form SL in the total amount of SL is less than 45 mass % (solid equivalent).

The method for collecting the lactone-form/acid-form SL-containing composition from the liquid culture of the SL-producing yeast may be a method widely known in the art as long as the advantageous effect of the present invention is not hindered, and examples thereof include a method described in JP2003-009896A (Patent Literature 3), etc. Since such a method controls the solubility of SL with respect to water by adjusting the pH of the liquid culture of the SL-producing yeast or the SL-containing fraction prepared therefrom, the lactone-form/acid-form sophorolipid-containing composition can be prepared as a compound hydrated by about 50%.

The partially purified acid-form sophorolipid-containing composition used as the material for production method A (and production method B) is prepared through hydrolysis of the lactone-form/acid-form sophorolipid-containing composition to open the lactone ring of the lactone-form SL, such that the contained amount of the acid-form SL in the total amount of SL becomes not less than 78 mass %. In addition, as a result of the hydrolysis, the number of types of sophorolipid homologs, for example, 30 types or more, contained in the lactone-form/acid-form sophorolipid-containing composition can be simplified to about four types.

For the hydrolysis, a method widely known in the art can be used as long as the advantageous effect of the present invention is not hindered. For example, alkali hydrolysis can be suitably conducted using bases such as alkanolamine, or a phosphate, a carbonate, or a metal salt (sodium, potassium, calcium and magnesium, etc.) of a hydroxide. Furthermore, it is possible to use various catalysts, for example, an alcohol or the like. The temperature, pressure, and time period for conducting the alkali hydrolysis can be configured as appropriate as long as the advantageous effect of the present invention is not hindered. However, it is preferable to use a temperature, pressure and time period allowing efficient progression of the hydrolysis of the lactone-form SL while inhibiting side reactions such as degradation and chemical modification of the acid-form SL which is the intended product. From this standpoint, the reaction temperature is ordinarily in a range of approximately 30° C. to 120° C., and preferably approximately 50° C. to 90° C. The pressure is ordinarily in a range of approximately 1 atm to 10 atm, and preferably approximately 1 atm to 2 atm. The reaction time is ordinarily in a range of approximately 10 minutes to 5 hours, and preferably approximately 1 hour to 3 hours. Furthermore, the time period for conducting the alkali hydrolysis can be configured as appropriate depending on the amount, concentration, etc., of the lactone-form SL in the lactone-form/acid-form sophorolipid-containing composition that is to be processed.

Furthermore, the partially purified acid-form sophorolipid-containing composition used for producing the high-purity acid-form SL-containing composition of the present invention may be obtained from a fermentative production method of selectively producing only the acid-form SL in a single step as described in, for example, JP2008-247845A (Patent Literature 4), etc. In addition, the product obtained from the fermentative production method may be additionally treated with an alkali.

(b) Step (i)

Step (i) is a step of adjusting the pH of the partially purified acid-form SL-containing composition to an acidic range. This can be referred to as a preparation step for an acidified partially purified acid-form SL-containing composition.

From the standpoint of effectively removing impurities such as fermentation by-products in a later step and obtaining the high-purity acid-form SL-containing composition at a high yield, the acidic range is preferably lower than about pH 6 since the pKa value of the acid-form SL is pH 6.1 to 6.4.

FIG. 1 shows the behavior (protonated acid-form SL←→ionized acid-form SL) of the high-purity acid-form SL-containing composition in a range of pH 2 to 9.5. Here, the protonated acid-form SL corresponds to an acid-form SL having a hydrogen atom bound to a carboxyl group, and the ionized acid-form SL corresponds to an acid-form SL in which the hydrogen atom is dissociated. As can be understood here, approximately pH 6.1 is a boundary wherein the ionized acid-form SL becomes predominant over the protonated acid-form SL in the pH range higher than pH 6.1, and the protonated SL becomes predominant over the ionized SL in the pH range lower than pH 6.1.

Although it is not particularly limited, the acidic range in step (i) of production method A is preferably not higher than about pH 5. More specifically, the pH is not lower than about pH 1 but lower than pH 6, and preferably about pH 1 to 5, and more preferably about pH 1 to 4.5. The pH is particularly preferably about 1 to 4.

The method for adjusting the partially purified acid-form SL-containing composition to the acidic range is not particularly limited as long as the advantageous effect of the present invention is not hindered, and a method widely known in the art can be used. Ordinarily, a method of adjusting the pH of the partially purified acid-form sophorolipid-containing solution by using a pH regulator can be used. Examples of the pH regulator that can be used include: inorganic acids such as sulfuric acid, hydrochloric acid, nitric acid, phosphoric acid, boric acid, and hydrofluoric acid; and organic acids such as formic acid, acetic acid, malic acid, citric acid, oxalic acid, glutamic acid, and aspartic acid.

(c) Step (ii-a)

Step (ii-a) subjects an acidified partially purified acid-form SL-containing composition obtained in step (i) to chromatography to acquire the intended high-purity acid-form SL-containing composition.

From the standpoint of isolation efficiency, the acidified partially purified acid-form SL-containing composition that is subjected to chromatography is preferably a liquid having a viscosity of approximately 5 to 50 mPa·S; and is more preferably a liquid having a viscosity of approximately 5 to 20 mPa·S. When the viscosity of the acidified partially purified acid-form SL-containing composition obtained in step (i) is high, it is preferable to adjust its viscosity within the range described above before subjecting it to chromatography. The method for adjusting the viscosity is not particularly limited as long as the advantageous effect of the present invention is not hindered; and diluting the composition with ethanol, water (e.g., purified water), or a mixture thereof is preferable when adverse effects against the human body and environment are taken into consideration.

It should be noted that the viscosity value of the acidified partially purified acid-form SL-containing composition is a value obtained when measurement is conducted with the following method and conditions.

Viscosity Measuring Conditions

Viscosity is measured based on JIS Z8803-2011. Specifically, 90 g of the sample is added to a 100-ml bottle made of polypropylene (PP bottle), and is warmed at 30° C. for 30 minutes. After confirming that the temperature has reached 30° C., the viscosity is measured using a model BII viscometer (manufactured by Toki Sangyo Co., Ltd., Model BL, No. 2/60 rpm).

Chromatography is a separation method utilizing the structure of SL, which is amphiphilic. Generally, as the filler (adsorbent) used as the stationary phase, any of those known in the art can be used, including silica gel, octadecyl silica gel (ODS) resins, ion-exchange resins, synthetic adsorbents, etc. The chromatography used in the present invention is preferably partition chromatography, in particular, reverse phase chromatography. With reverse phase chromatography, an eluent (mobile phase) that is highly safe for the environment and human body can be used.

When reverse phase chromatography is used as the chromatography, ODS resin or the like is preferably used as the filler. When ODS resin having a chemical modification of a hydrophobic octadecyl group or the like on a silica gel support is used, it becomes possible to efficiently purify the acid-form SL from the acidified partially purified acid-form SL-containing composition by using a hydrophobic interaction with an alkyl side-chain of SL, and to acquire a highly pure acid-form SL-containing composition. As the eluent (mobile phase) of the reverse phase chromatography, from the standpoint of isolation efficiency, etc., a solvent whose polarity is stronger than that of the filler used in the stationary phase is preferably used. Although examples of the eluent include a mixture of water and a lower alcohol, such as methanol and ethanol, a mixture of water and ethanol is preferable from the standpoint of safety and the environment. As described above, step (ii-a) by the method (production method A) of the present invention is a preferable method since it uses a solvent that is less hazardous against the environment and human body, and can be widely used industrially.

It should be noted that, in the chromatography employed in the present invention, a pH regulator such as, for example, acetic acid, formic acid, and tetrahydrofuran, is preferably not added to the eluent. An added pH regulator is difficult to remove from an SL collection fraction, and the pH regulator may degrade the glycosidic bond in SL and reduce the purity. Furthermore, usage of an eluent containing an organic solvent such as chloroform which may harm the human body, the environment, etc., is not preferable from the standpoint of safety, etc.

Reverse phase chromatography is not particularly limited as long as the advantageous effect of the present invention is not hindered. For example, when an aqueous ethanol solution is used as the eluent, it is possible to apply the acidified partially purified acid-form SL-containing composition to the filler (stationary phase), elute and wash away other components (impurities) while having the acid-form SL adsorbed on the filler by pouring the eluent (aqueous ethanol solution) during which the ethanol concentration is intermittently or continuously increased in a range of approximately not lower than 10% but lower than 60% (meaning vol %, the same applies hereinafter), and then collect a fraction (acid-form SL fraction) containing the acid-form SL by pouring an eluent (aqueous ethanol solution) whose ethanol concentration is approximately 70 to 90% thereon. Specific examples include the following method.

(1) A column is equilibrated by supplying from the topmost part of the column (hereinafter, separation-column overhead) an eluent having a concentration of approximately 10 to 30% (e.g., an eluent (aqueous ethanol solution) whose ethanol concentration is approximately 10 to 30%).

(2) The acidified partially purified acid-form SL-containing composition is added from the separation-column overhead.

(3) The eluent having a concentration of approximately 10 to 40% is poured from the separation-column overhead. With this process, salts and components, including mainly acetic acid, which become a cause of unpleasant odors, can be eluted.

(4) The eluent having a concentration of approximately not lower than 40% but lower than 60% is poured from the separation-column overhead. With this process, pigments and components, including mainly acetic acid, which become a cause of unpleasant odors, can be eluted.

(5) The eluent having a concentration of approximately 70 to 90% is poured from the separation-column overhead to elute and collect an acid-form SL fraction.

It should be noted that, in each of the steps of (1), (3), and (4), the ethanol concentration of the eluent may be chronologically increased within the above described concentration range (gradient elution method), or may be maintained at the same concentration (step-wise elution method). The latter step-wise elution method is preferable, and an illustrative method is, for example, as follows. To a column filler equilibrated with an aqueous ethanol solution having an ethanol concentration of 10% (step (1)), the acidified partially purified acid-form SL-containing composition is added (step (2)), a certain amount of an aqueous ethanol solution having an ethanol concentration of 10% is poured (step (3)), a certain amount of an aqueous ethanol solution having an ethanol concentration of 50% is poured (step (4)), and then an aqueous ethanol solution having an ethanol concentration of 70% is poured to elute and collect the intended acid-form SL fraction (step (5)). Furthermore, it is possible to omit step (3) described above, and, as step (4), pouring of the aqueous ethanol solution having an ethanol concentration of approximately not lower than 40% but lower than 60% may be started after step (2). In this case, since salts and pigment components can be simultaneously eluted and removed in addition to acetic acid that becomes a cause of an irritative odor, the elution step can be shortened and the amount of ethanol used can be reduced.

When additives (pH regulators) such as acid and alkali are not added to the eluent, the eluent eluted from the column can be used again after an easy distillation operation, such as distillation using an evaporator. Furthermore, after eluting and collecting the acid-form SL fraction, if desired, an aqueous ethanol solution having an ethanol concentration of approximately 90 to 100% may be poured from the separation-column overhead. With this operation, since hydrophobic substances such as fatty acids can be eluted and removed from the column filler, the filler can be reused.

As shown in later described Examples 1 and 2, and Test Examples 1, 2, and 4 to 7, when the production method (production method A) of the present invention is used and steps (i) and (ii-a) are combined in this order, acetic acid that becomes a cause of an irritative odor is removed, and a high-purity acid-form SL-containing composition that substantially does not contain acetic acid can be obtained. Since other odor components derived from fermentation by-products are significantly removed from the high-purity acid-form SL-containing composition, and since the contained amount of those in the composition is reduced, the composition is odorless or has an extremely faint odor.

(III-2) Production Method B (a) Material (Partially Purified Acid-Form Sophorolipid-Containing Composition)

In production method B, the aqueous solution containing a partially purified acid-form sophorolipid (partially purified acid-form SL-containing composition) used as the material is identical to the partially purified acid-form SL-containing composition used in production method A. Therefore, the description of "(a) Material (partially purified acid-form sophorolipid-containing composition)" of (III-1) production method A described above can be incorporated herein by reference.

(b) Step (i)

In production method B, the operation conducted in step (i) is basically identical to the operation in step (i) used in production method A. Therefore, the description of "(b) Step (i)" of (III-1) production method A described above can be incorporated herein by reference.

However, the acidic condition of the partially purified acid-form SL-containing composition is preferably in a range of not higher than pH 6, more preferably not higher than about pH 5, and further preferably not higher than about pH 4. The lower limit of the pH value is not particularly limited, and examples thereof ordinarily include about pH 1.

As shown in Test Example 3, for the gelling of the acidified partially purified acid-form SL-containing composition, it is necessary to appropriately combine the temperature condition and pH condition of the acidified partially purified acid-form SL-containing composition. Therefore, it is necessary to change the temperature condition used in the next step (ii-b) depending on the pH condition of the acidified partially purified acid-form SL-containing composition.

(c) Step (ii-b)

Step (ii-b) is a step of leaving the acidified partially purified acid-form SL-containing composition obtained in step (i) to stand under a low-temperature condition to gel the composition.

Here, as described above, the low-temperature condition has to be adjusted depending on the pH of the acidified partially purified acid-form SL-containing composition obtained in step (i). As shown in Test Example 3, when the pH of the acidified partially purified acid-form SL-containing composition is, for example, not higher than 4, examples of the temperature condition include not higher than 15° C., and preferably not higher than 10° C. In addition, when the pH of the acidified partially purified acid-form SL-containing composition is, for example, higher than 4 but not higher 5, examples of the temperature condition include not higher than 10° C., preferably not higher than 0° C., and more preferably not higher than −10° C. Furthermore, when the pH of the acidified partially purified acid-form SL-containing composition is, for example, higher than 5 but not higher than 6, examples of the temperature condition include not higher than −10° C., and preferably not higher than −25° C. Still further, when the pH of the acidified partially purified acid-form SL-containing composition is, for example, higher than 6 but not higher than 7, examples of the temperature condition include not higher than −20° C., and preferably not higher than −25° C.

In view of the fact that water will freeze at a temperature of 0° C. or lower, it is preferable to use a pH condition for performing the gelling at a temperature not lower than 0° C. Therefore, in production method B, the acidic condition to which the partially purified acid-form SL-containing composition is adjusted in step (i) is configured to be not higher than pH 4, preferably about pH 1 to 4, and more preferably about pH 2 to 4, and, in step (ii-b), the acidified partially purified acid-form SL-containing composition is preferably left to stand under a low-temperature condition of not higher than 15° C. (0 to 15° C.), and preferably not higher than 10° C. (0 to 10° C.).

The acidified partially purified acid-form SL-containing composition is gelled when left to stand under these conditions for one-half to several days, and a gel-form acidic partially purified acid-form SL-containing composition can be collected.

The gel-form partially purified acid-form SL-containing composition can be collected by removing a liquid layer through solid-liquid separation in accordance with a hitherto known method such as filtering as shown in Example 4. However, by further washing the obtained solid fraction with a cold solvent and washing away impurities contained in the partially purified acid-form SL-containing composition, a high-purity acid-form SL-containing composition with even higher purity can be acquired. The temperature of the cold solvent is sufficient if it is a temperature that does not compromise gelling of the high-purity acid-form SL-containing composition, and examples thereof include not higher than 15° C., and preferably 0 to 10° C. Here, as the cold solvent, one that does not compromise gelling of the high-purity acid-form SL-containing composition may be used, and examples thereof include water, organic solvents such as lower alcohols (ethanol, propylene alcohol, etc.) and acetone, or a mixture of water and an organic solvent. The cold solvent is preferably water, or a mixture with an organic solvent. It should be noted that the organic solvent is preferably ethanol, and when it is used as a mixture with water, 10 vol % or lower can be illustrated as the concentration.

Although the washing with the cold solvent is not limited, it is preferable to conduct the washing repeatedly. Furthermore, although not limited, as the total amount of the cold solvent used for the washing, a 2- to 50-fold amount of the volume of the gel-like material that is to be washed can be given as an example.

As shown in Example 4 and Test Examples 1 and 2 described later, when the production method (production method B) of the present invention is used and steps (i) and (ii-b) are combined in this order, acetic acid that becomes a cause of an irritative odor is removed, and a high-purity acid-form SL-containing composition that substantially does not contain acetic acid can be obtained. Since other odor components derived from fermentation by-products are significantly removed from the high-purity acid-form SL-containing composition, and since the contained amount of those in the composition is reduced, the composition is odorless or has an extremely faint odor.

(d) Steps (iii) and (iv)

The following steps (iii) and (iv) are steps for distilling the high-purity acid-form SL-containing composition obtained via steps (i) and (ii-a) (production method A) or steps (i) and (ii-b) (production method B), and drying the obtained distillation residue:

(iii) distilling a liquid high-purity acid-form SL-containing composition obtained via the steps of (i) and (ii) ((ii-a) or (ii-b)); and (iv) precipitating an acid-form SL from a residual liquid obtained from the distillation.

Step (iii) is a step of distilling a liquid high-purity acid-form SL-containing composition (high-purity acid-form SL-containing solution), which contains water, obtained via step (ii), to adjust the concentration of the acid-form SL contained in the high-purity acid-form SL-containing solution. Furthermore, this is also a step of distilling off organic solvents if organic solvents such as ethanol are intermixed in the high-purity acid-form SL-containing solution obtained via step (ii).

It should be noted that, with production method A, it is possible to use an elution fraction of the acid-form SL obtained from the chromatography in step (ii-a) directly as the high-purity acid-form SL-containing solution for step (iii). Furthermore, with production method B, the gelled object obtained in step (ii-b) may be warmed and dissolved, and used for step (iii) as the high-purity acid-form SL-containing solution.

The concentration of the acid-form SL contained in the liquid remaining after distillation (distillation residual liquid) is not particularly limited as long as the advantageous effect of the present invention is not hindered, and examples thereof include ordinarily not higher than about 50 mass %, preferably not higher than 40 mass %, more preferably not higher than 30 mass %, and particularly preferably about 20 mass %. By adjusting the concentration of the acid-form SL as such, advantageous effects can be obtained such as being able to easily form a powder or obtain a fine powder when used in the next precipitation (powdering) step.

The distillation method is not particularly limited as long as the advantageous effect of the present invention is not hindered, and a distillation method known in the art can be used. Examples of the distillation method include molecular distillation, vacuum distillation, steam distillation, etc. From an industrial standpoint, vacuum distillation is preferable.

Step (iv) is a step of precipitating the acid-form SL from the distillation residual liquid obtained in step (iii). In this step, the high-purity acid-form SL-containing composition of the present invention can be made into a powder.

Although examples of the method for precipitating the acid-form SL generally include a freeze-drying method (lyophilization method), a recrystallizing method, a spray-drying method, and the like, a spray-drying method is preferably performed in the present invention. Since the acid-form SL of the present invention is chemically very stable and resistant to heat, and poses a low risk of structural change, it becomes possible to efficiently produce the high-purity acid-form SL-containing composition of the present invention by utilizing the spray-drying method, which enables continuous production.

For the spray-drying method, although a diluting agent may or may not be used, it is preferably to not use a diluting agent from the standpoint of obtaining a highly pure acid-form SL powder. Although the conditions of the spray-drying method are not particularly limited as long as the advantageous effect of the present invention is not hindered, when it is processed at a high temperature and high rotation (e.g., temperature of not lower than 100° C. and a rotational speed of not lower than 12,000 rpm), a high-purity acid-form SL-containing composition that is highly fluid and in a form of powder which is less lumpy can be obtained.

(e) Steps (v) and (vi)

The following steps (v) and (vi) are steps of solidifying, through cooling, the high-purity acid-form SL-containing composition obtained via steps (i) and (ii-a) (production method A) or steps (i) and (ii-b) (production method B), and drying thereof:

(v) solidifying, through cooling, the high-purity acid-form SL-containing composition obtained via step (i) and step (ii-a) or (ii-b); and (vi) drying the cooling-solidified object.

Step (v) includes a step of freeze-solidifying the liquid high-purity acid-form SL-containing composition (high-purity acid-form SL-containing solution), which contains water, obtained via step (ii), and step (vi) includes a step of drying the freeze-solidified object. In this case, the series of steps (v) and (vi) are freeze-drying steps (lyophilization steps). With the present step, the high-purity acid-form SL-containing composition of the present invention can be made into a solid state (lyophilized state).

It should be noted that, with production method A, it is possible to use an elution fraction of the acid-form SL obtained from chromatography in step (ii-a) directly for step (v), or to once concentrate the elution fraction and then use it for step (v). Furthermore, with production method B, the gelled object obtained in step (ii-b) may be directly used for step (v).

If desired, the production method of the present invention may have a step of further purification with means known in the art, such as filtering with activated carbon or an adsorption resin. By having such a step, a further high-purity composition that is preferable in terms of not only its odor but also in terms of its color, etc., can be obtained. Although the purification step may be conducted during any of the steps in the production method of the present invention, the purification step is preferably conducted between steps (i) and (ii-a) or between steps (i) and (ii-b) from the standpoint of efficiency, etc. Furthermore, particularly when the chromatography in step (ii-a) is column chromatography, conducting the purification step beforehand has an advantage of reducing the load applied to the column.

The thus obtained solid (e.g., powder) high-purity acid-form SL-containing composition has excellent preservation stability, can be applied to various formulations irrespective of whether the formulation is water based or oil based as shown in the Examples described later, and is convenient in terms of handling.

EXAMPLES

The present invention is described below more specifically with reference to Examples and Test Examples. However, the invention is not limited thereto or thereby, and various modifications are possible within the spirit of the present invention by a person skilled in the art. In the following Examples and Test Examples, sophorolipid is also referred to as "SL."

In the following Reference Production Examples and Examples 1 to 3, the dry residue, ethanol soluble matter, saponification value, and viscosity were determined by the following methods.

(1) Evaporation Residue (wt %)

The evaporation residue was measured in accordance with the second method of JIS K0067-1992. Two grams of each sample was placed in a 100-mL beaker with a known weight and heated at 105° C. for 3 hours and then allowed to cool in a desiccator. The weight of the residue in the beaker was measured. Drying at 105° C. and cooling in the desiccator were repeated until the weight (g) of the residue became constant. The evaporation residue (wt %) of each sample was calculated according to the following formula.

Evaporation residue (wt %)=Weight (g) of the residue in the beaker/Sampling amount (g)×100   Mathematical Formula 2

(2) Ethanol Soluble Matter (wt %)

The ethanol soluble matter in each sample was measured according to JIS K3362-2008. Two grams of each sample was placed into a 100-mL beaker and heated at 105° C. for 2 hours, while occasionally mixing with a glass rod to remove low volatile components. Then, 30 mL of ethanol (95) was added and the resulting mixture was heated on a water bath for 30 minutes to dissolve the residue in the beaker. The warm solution, as is, was filtered through a glass filter and collected in a 200-mL recovery flask with a known weight. Then 20 mL of ethanol was added again to the residue in the beaker and the residue was dissolved while heating on a water bath. The resulting warm solution was filtered through a glass filter and the beaker and glass filter were washed well with hot ethanol to collect the filtrate in the recovery flask. After the collected filtrate was allowed to cool to room temperature and ethanol was distilled off by an evaporator, the residue was dried at 105° C. for 1 hour and then allowed to cool in a desiccator. The weight (g) of the residue in the recovery flask was measured. The ethanol soluble matter (wt %) was calculated according to the following formula.

Ethanol soluble matter (wt %)=Weight (g) of the residue in the recovery flask/Sampling amount (g)×100   Mathematical Formula 3

(3) Saponification Value

The saponification value was measured according to the Standard Methods for the Analysis of Fats, Oils and Related Materials (2.3.2.1-1996).

(4) Viscosity

The viscosity was measured according to JIS Z8803-2011. Ninety grams of each sample was placed in a 100-mL polypropylene bottle (PP bottle) and heated at 30° C. for 30 minutes. After confirmation that the temperature reached 30° C., the viscosity was measured with a Brookfield II viscometer (produced by Toki Sangyo Co., Ltd., Model BL, No. 2/60 rpm).

(5) HPLC Analysis

The table below shows the HPLC analysis conditions used in the following Examples and Test Examples.

TABLE 1

| Device | LC-10 AD-VP (produced by Shimadzu Corporation) |
|---|---|
| Column | Inertsil ODS-3 (4.6 mm × 250 mm, produced by GL Sciences Inc.) |
| Column temperature | 40° C. |
| Mobile phase | Liquid A: Distilled water
Liquid B: Methanol containing 0.1% formic acid
Gradient: Proportion of liquid B: 30% → 100%/0 → 60 minutes |
| Mobile phase flow rate | 1.0 mL/min |
| Sample concentration | 10 mg/mL (prepared using methanol) |
| Injection volume | 10 μL |
| Detector | Detector: Evaporative light scattering detector ELSD-LT II (produced by Shimadzu Corporation)
Temperature: 40° C.
Gain: 5
Nebulizer gas: nitrogen
Gas pressure: 350 kPa |

Reference Production Example 1

Extraction of Sophorolipid (Preparation of a Lactone-Form/Acid-Form SL-Containing Composition)

A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of a yeast extract (produced by Asahi Food & Healthcare Co., Ltd., product name: Meast Powder N) was used as a culture medium. *Candida bombicola* ATCC22214 was cultured in the medium while shaking at 30° C. for 2 days. This was used as a pre-culture fluid.

The pre-culture fluid was inoculated in a proportion of 4% into a main culture medium (3 L) placed in a 5-liter fermenter, and then cultured at 30° C. at an aeration rate of 0.6 vvm for 6 days for fermentation. The main culture medium contained, per liter, 100 g of aqueous glucose, 50 g of palm olein (produced by NOF Corporation, product name: Palmary 2000), 50 g of oleic acid (produced by ACID CHEM, product name: Palmac 760), 1 g of sodium chloride, 10 g of monopotassium phosphate, 10 g of magnesium sulfate heptahydrate, 2.5 g of yeast extract (produced by Asahi Food & Healthcare Co., Ltd., product name: Meast Powder N), and 1 g of urea (pH 4.5 to 4.8 before sterilization).

On the 6th day from the start of culturing, the fermentation was stopped. The culture fluid removed from the fermenter was heated, then returned to room temperature, and allowed to stand for 2 to 3 days. As a result, the culture was separated into the following three layers in sequence from the bottom up: a liquid brown precipitate layer; a milky white solid layer presumably mainly comprising the cells; and a supernatant. After the supernatant was removed, industrial water or groundwater was added in an amount equal to the amount of the supernatant removed. While the resulting mixture was stirred, a 48 mass % sodium hydroxide solution was gradually added to achieve a pH of 6.5 to 6.9, and SL contained in the culture fluid was solubilized.

The resulting product was centrifuged by a tabletop centrifuge (Westfalia: produced by Westfalia separator AG) to precipitate milky white solids, and the supernatant was collected. While the collected supernatant was stirred, 62.5 mass % sulfuric acid was gradually added to achieve a pH of 2.5 to 3.0, and the SL was insolubilized again. After this was allowed to stand for 2 days, the supernatant was removed by decantation as much as possible, thus obtaining the residue as a "lactone-form/acid-form SL-containing composition" (about 50% water content, Reference Production Example product 1). The "lactone-form/acid-form SL-containing composition" comprises less than 45 mass % of acid-form SL and at least 55 mass % of lactone-form SL. The Table below shows the physical properties of the obtained "lactone-form/acid-form SL-containing composition."

TABLE 2

| Presence of odor | Acidulous odor |
|---|---|
| Appearance | Brown transparent viscous liquid |
| pH (25° C., glass electrode method) | 3.0 |
| Viscosity (mPa · s) | 533 |
| Evaporation residue (wt %) | 58 |
| Saponification value | 138 |

Reference Production Example 2

Partial Purification of the Acid-Form Sophorolipid (Preparation of a Partially Purified Acid-Form SL-Containing Composition)

An aqueous sodium hydroxide solution was added to the lactone form/acid-form SL-containing composition obtained in the above Reference Production Example 1 to achieve pH 12 and the mixture was heated at 80° C. for 2 hours to perform hydrolysis (alkali hydrolysis). After the hydrolysate was returned to room temperature, the generated insolubles were removed by filtration, and the filtrate was obtained as a "partially purified acid-form SL-containing composition" (Reference Production Example product 2). The "partially purified SL-containing composition" comprises at least 78 mass % of acid-form SL and less than 22 mass % of lactone-form SL, based on the total amount of acid-form SL and lactone-form SL as 100 mass %. The Table below shows the physical properties of the "partially purified acid-form SL-containing composition".

TABLE 3

| Presence of odor | A distinctive odor |
|---|---|
| pH | 7.7 |
| Viscosity (mPa · s) | 9.7 |
| Evaporation residue (%) | 33 |
| Ethanol soluble matter (%) | 32.2 |

Example 1

Production of a High-Purity Acid-Form Sophorolipid-Containing Composition (Liquid)

Sulfuric acid (9.8M aqueous solution) was added to adjust the partially purified acid-form SL-containing composition obtained in Reference Production Example 2 to pH 3.2 (an acidified partially purified acid-form SL-containing composition).

This was subjected to reverse phase column chromatography under the following conditions.

Solid phase: C18 column (COSMOSIL 40C18-PREP, produced by Nacalai Tesque, Inc., 15 kg)
Mobile phase: 10% to 70% ethanol aqueous solution.

More specifically, 1.2 kg of the acidified partially purified acid-form SL-containing composition (Reference Production Example product 2) adjusted to pH 3.2 was added to a C18 column (in an amount of about 3% as ethanol soluble matter, based on the solid phase loading amount). By adding 20 L of a 10% ethanol aqueous solution and then 35 L of a 50% ethanol aqueous solution, water-soluble impurities (odor, salts, and some pigment substances) were removed by elution. Subsequently, 30 L of a 70% ethanol aqueous solution was supplied to the column to elute a desired acid-form SL-containing fraction from the C18 column.

The obtained fraction was analyzed by HPLC with an evaporative light scattering detector and by FTIR (a Fourier transform infrared spectrometer Spectrum™ 100, ATR method). The simplified chemical structure, complete cleavage of the lactone moiety, and total desorption of acetyl were observed. These results confirmed that acid-form SL is contained in a high purity (a high-purity acid-form SL-containing solution).

The high-purity acid-form SL containing solution thus obtained was a colorless transparent solution having an acid-form SL concentration of 1 mass %, pH 3.3, an ethanol concentration of 70 vol %, a viscosity of 15.3 mPa·s, and an ethanolic odor (Example product 1).

Example 2

Preparation of a High-Purity Acid-Form Sophorolipid (Powder)

The high-purity acid-form SL-containing solution (Example product 1) obtained in Example 1 was subjected to an evaporator (produced by Toyo Chemical Food Plant Co., Ltd.) to distill off the solvent (ethanol) and concentrate the solution. The obtained concentrate was a transparent solution having an acid-form SL concentration of 15 mass %, pH 3.3, an ethanol concentration of 5 vol % or less, a viscosity of 10.2 mPa·s, and an ethanolic odor.

Figure 2:
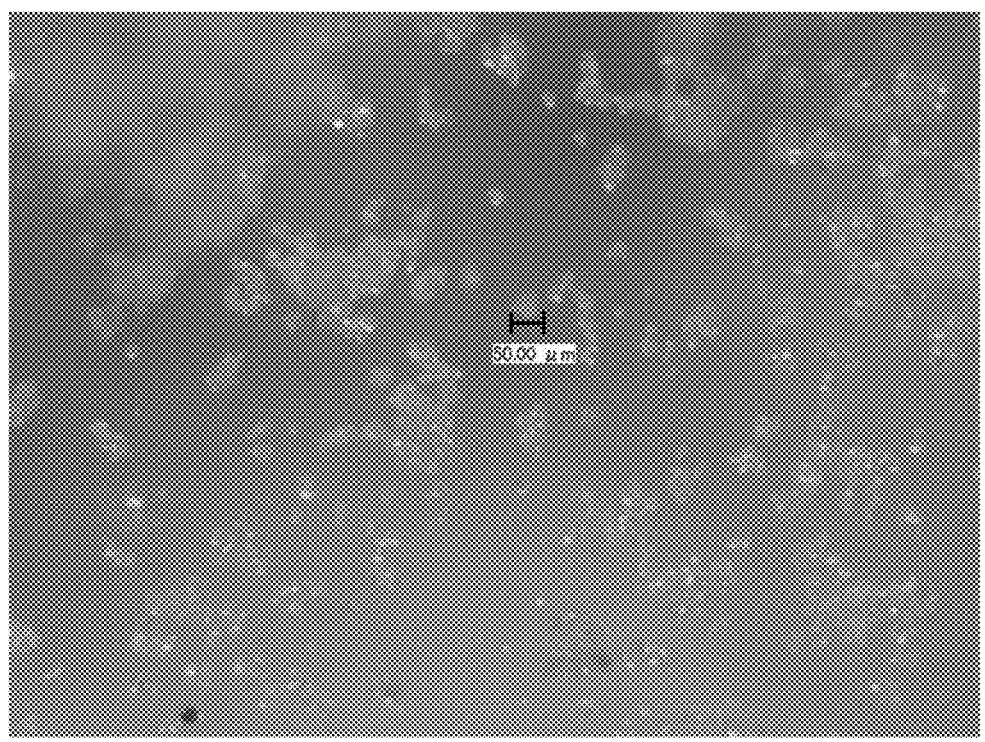
FIG. 2 is a microscope picture of a high-purity acid-form SL-containing composition (powder) of the present invention.

The concentrate was subjected to a spray dryer (drying pulverizer) (model: R-3, made of SUS304, water evaporation capacity: Max. 5 kg/h, produced by Sakamotogiken Co., Ltd.) to obtain a dry powder. The following spray drying conditions were used: atomizer: 12,000 rpm; and temperature in the chamber: 105° C. As a result, a fine powder was obtained (Example product 2). The obtained powder was measured using a microscope (Digital Microscope VHX-900, produced by Keyence Corporation) at 200× magnification (FIG. 2). The recovery rate obtained by this method was 25% on average for three tests, based on 1.2 kg of the acid form SL-containing composition adjusted to pH 3.2 (C18 column feed material in Example 1).

TABLE 4

Shape and diameter of the sieve frame: Cylindrical, 200 mm
Type of sieve screen: Flat
Screening method: Dry, mechanical screening
Sampling amount (g): 199.8

| Particle diameter range (μm) | Weight (%) |
|---|---|
| (1) 1000 < X | 2.8 |
| (2) 710 < X < 1000 | 1.9 |

TABLE 4-continued

Shape and diameter of the sieve frame: Cylindrical, 200 mm
Type of sieve screen: Flat
Screening method: Dry, mechanical screening
Sampling amount (g): 199.8

| Particle diameter range (μm) | Weight (%) |
|---|---|
| (3) 500 < X < 710 | 2.2 |
| (4) 355 < X < 500 | 2.3 |
| (5) 250 < X < 355 | 3.2 |
| (6) 180 < X < 250 | 17.7 |
| (7) 150 < X < 180 | 15.5 |
| (8) 100 < X < 150 | 10.8 |
| (9) X < 100 | 43.6 |

The physical properties of the obtained high-purity acid-form SL-containing composition (powder) were as shown in the Table below. Based on 100 mass % of SL contained in the high-purity acid-form SL-containing composition (powder), acid-form SL accounted for 99 mass % or more. The composition had no unpleasant odor that is characteristic to fermentation byproducts, and removal of some pigment components was also confirmed.

TABLE 5

| Presence of odor | Odorless or slight distinctive odor |
|---|---|
| Color | White or slightly yellow powder |
| Evaporation residue (%) | 99.2 |

Table 6 shows the results of the stability test of Example product 2. In the stability test, physical properties of Example product 2 were investigated after storage for 1 month under low-temperature conditions (−5° C.) or after storage for 1 month under high-temperature conditions (50° C.) (both in the dark).

TABLE 6

| Item | Before the stability test | After the stability test (at −5° C. for 1 month) | After the stability test (at 50° C. for 1 month) |
|---|---|---|---|
| Presence of odor | Odorless or slight distinctive odor | Odorless or slight distinctive odor | Odorless or slight distinctive odor |
| Color | White or slightly yellow powder | White or slightly yellow powder | White or slightly yellow powder |
| Evaporation residue (%) | 99.2 | 99.1 | 99.1 |

These results show that the high-purity acid-form SL-containing composition (powder) obtained above exhibits extremely high long-term stability with no color change and no odor change under any of the high-temperature and low-temperature conditions. Further, as a result of HPLC analysis of the powder after the stability test, it was found that the high-purity acid-form SL-containing composition (powder) did not change in chemical structure, compared to the structure before the stability test. It was also found that the composition is not susceptible to microbial contamination because the water content is low.

Example 3

Example product 2 (high-purity acid-form SL-containing composition (powder)) was dissolved in distilled water heated at about 60° C. until the acid-form SL concentration became about 15 mass %, thus obtaining an aqueous solution having pH 3.0. It was found that when this aqueous solution was cooled to 4° C., the solution gelled without crystallization. This phenomenon was considered to be attributable to the conformation or network of the acid-form SL formed in the solution.

Example 4

Preparation of a High-Purity Acid-Form Sophorolipid-Containing Composition (Gel)

100 g of the partially purified acid-form SL-containing composition obtained in Reference Production Example 2 was mixed with 9 g of a 62.5% aqueous sulfuric acid solution to achieve a pH of about 3, and the mixture was stored in a refrigerator (about 7° C.) overnight. After the storage, the obtained gel was transferred to a mortar, and 200 g of cooling water (distilled water refrigerated in a refrigerator) was added. The gel was mashed into a suspension. This suspension was transferred to a glass funnel and filtered to remove the cooling water. After 200 mL of cooling water was added to the obtained filtrate (filtration residue), the resulting mixture was mixed with a scoopula and dispersed. The dispersion was filtered under reduced pressure and the cooling water was removed. This operation was repeated 5 times, and washing was performed with cooling water in a total amount of 1,000 mL. The obtained wash in the glass funnel was heated in a 50° C. incubator and dissolved. This solution was filtered under reduced pressure and the filtrate was collected. The filtrate was solidified through cooling in a freezer (−30° C.) and then pulverized by freeze-drying.

Similar to Example product 2 (high-purity acid-form SL-containing composition), the obtained powder did not have an unpleasant odor that is characteristic to fermentation byproducts. This confirmed that a high purity acid-form SL-containing composition from which impurities (odor components) had been significantly removed was also obtained by the method of Example 4 comprising cooling and gelling the partially purified acid-form SL-containing composition obtained in Reference Production Example 2 under acidic conditions, instead of using the column purification of Examples 1 and 2. The recovery rate obtained by this method was 16.2% on average for three tests, based on 100 g of the acid-form SL-containing composition.

Comparative Example 1

Ethyl acetate and water were added to the lactone-form/acid-form SL-containing composition obtained in Reference Example 1 and an ethyl acetate layer was extracted. The extracted ethyl acetate layer was concentrated using an evaporator, and an aqueous sodium hydroxide solution was added to adjust the concentrate to pH 12. Subsequently, this solution was heated at 80° C. for 2 hours and hydrolyzed to obtain an acid-form SL-containing composition (Comparative Example product 1).

Comparative Example 2

Hexane was added to the lactone-form/acid-form SL-containing composition obtained in Reference Production Example 1, and an extracted hexane layer was removed. After 100 g of a 5M aqueous sodium hydroxide solution was added to 50 g of the residue (SL fraction), the mixture was subjected to treatment at 80° C. for 2 hours and hydrolyzed. Subsequently, the hydrolysate was allowed to cool to room temperature and then adjusted to pH 2 with an aqueous HCL solution, thus precipitating acid-form SL. After the supernatant (aqueous layer) was removed, the precipitated acid-form SL layer was withdrawn, and the water was azeotroped with methanol to obtain an acid-form SL-containing composition (Comparative Example product 2).

Comparative Examples 3 to 5

An acid-form SL-containing composition (Comparative Example product 3) was produced in the same manner as in Example 1 except that the partially purified acid-form SL-containing composition obtained in Reference Production Example 2 was adjusted to pH 7.0 instead of pH 3.2 in Example 1. Acid-form SL-containing compositions (Comparative Example products 4 and 5) were produced in the same manner as in Comparative Example 3 except that the partially purified acid-form SL-containing composition was adjusted to pH 9.0 (Comparative Example 4) and pH 10.0 (Comparative Example 5), respectively, in place of pH 3.2. The Table below shows the SL recovery rates of Example product 1 and Comparative Example products 3 to 5. Example product 1 exhibited a recovery rate higher than that of Comparative Example products 3 to 5.

TABLE 7

|  | pH | Recovery rate (%) |
| --- | --- | --- |
| Example product 1 | 3.2 | 95 |
| Comparative Example product 3 | 7.0 | 60 |
| Comparative Example product 4 | 9.0 | 50 |
| Comparative Example product 5 | 10.0 | 48 |

Test Example 1

Measurement of Odor Components

The odor components in the acid-form SL-containing compositions obtained in the above Reference Production Examples, Examples, and Comparative Examples (Example product 2, Example product 4, Reference Production Example 1, and Comparative Example product 2) were analytically quantified using a "headspace gas chromatography with a hydrogen flame ionization detector (HS-GC-FID)."

(1) Experimental Method

One gram of ethanol soluble matter of each sample was placed in a 19-mL syringe vial (27 mm in waist diameter×55 mm in height×15 mm in inlet internal diameter). After 50 µL of a 5,000 ppm 1-butanol aqueous solution was added as an internal standard, a 5% sulfuric acid aqueous solution was added to make the total volume 3 mL. After the lid of the syringe vial was closed, the mixture was heated at 60° C. for 20 minutes or more to completely dissolve the solids of the sample, and the gas phase portion in the vial was equilibrated. 1 mL of the gas phase portion was collected using an MS-GLL500 microsyringe (produced by Ito Seisakucho Co., Ltd.) previously heated at 60° C. or higher, and supplied to a GC-2014 gas chromatograph under the following gas chromatography conditions.

GC Conditions

Capillary column: DB-WAX (30 m in length×0.25 mm in inner diameter×0.25 mm in film thickness)

Carrier gas: nitrogen (flow rate: 1.2 mL/min)

Elevated temperature conditions: 40° C. (for 5 minutes), 40 to 240° C. (8° C./min), 240° C. (for 5 minutes)
Vaporizing chamber temperature: 200° C.
Detector temperature: 270° C.
Sample injection method: splitless Quantification Method Quantification was carried out using an internal standard method. The acetic acid concentration (μg/mL) contained in 1 mL of the microsyringe was calculated by dividing the obtained acetic acid peak area value by the internal standard area. The total odor concentration (μg/mL) contained in 1 mL of the microsyringe was calculated by dividing the obtained total peak area value (from which the internal standard area value was subtracted) by the internal standard area.

Acetic acid concentration (μg/mL)=(Acetic acid peak area value/Internal standard area value)×250

Total odor concentration (μg/mL)=([Total area value−internal standard area value]/Internal standard area value)×250   Mathematical Formula 4

(2) Experimental Results

The table below shows the acetic acid concentration and the total amount of odor components (total odor concentration) of each sample (n=2) obtained by the above methods.

TABLE 8

| | Acetic acid concentration* (μg/mL) | Average acetic acid concentration (μg/mL) | Total odor concentration (μg/mL) | Average total odor concentration (μg/mL) |
|---|---|---|---|---|
| Example product 2 | 0 | 0 | 122 | 124 |
| | 0 | | 125 | |
| Example product 4 | 0 | 0 | 289 | 242 |
| | 0 | | 195 | |
| Reference Production Example product 1 | 313 | 301 | 2761 | 2764 |
| | 290 | | 2767 | |
| Reference Comparative Example product 2 | 531 | 509 | 1159 | 1189 |
| | 487 | | 1219 | |

*Acetic acid detection limit: 5 μg/mL

As is clear from the above results, the high purity acid-form SL-containing compositions of the present invention obtained in Examples 2 and 4 (Example product 2 and Example product 4) substantially contain no acetic acid that causes an irritative odor (detection limit: 5 μg/mL or less), and is also extremely low in the total amount of odor components. Thus, the compositions can be judged as being substantially odorless.

(3) Stability Over Time

After the above Example product 2 and Example product 4 (n=2) were stored at room temperature for several months (Example product 2: for 9 months and Example product 4: for 6 months), odor analysis was performed again, and the stability of the products over time was evaluated.

The Table below shows these results as well as the aforementioned results.

TABLE 9

| | Acetic acid concentration* (μg/mL) | Average acetic acid concentration (μg/mL) | Total odor concentration (μg/mL) | Average total odor concentration (μg/mL) |
|---|---|---|---|---|
| Example product 2 (before storage) | 0 | 0 | 122 | 124 |
| | 0 | | 125 | |
| Measured after storage at room temperature for 9 months | 0 | 0 | 180 | 179 |
| | 0 | | 178 | |
| Example product 4 (before storage) | 0 | 0 | 289 | 242 |
| | 0 | | 195 | |
| Measured after storage at room temperature for 6 months | 0 | 0 | 1077 | 1107 |
| | 0 | | 1137 | |

*Acetic acid detection limit: 5 μg/mL

The results confirmed that none of the samples generated acetic acid that causes an irritative odor even when stored at room temperature for a long period of time. The results further confirmed that although long-term storage tends to slightly increase the total odor amount of Example product 4, an increase in the total odor amount was significantly suppressed in Example product 2.

Test Example 2

Measurement of Physical Properties of Each Sample

The ignition residue, ester value, evaporation residue, drying loss, ethanol soluble matter, and infrared absorption spectrum of the acid-form SL-containing compositions obtained in the above Reference Production Examples, Examples, and Comparative Examples were measured.

(1) Summary of the Tests

TABLE 10

| Test item | Components to be measured | Measurement details | Method applied |
|---|---|---|---|
| Ignition residue (%) | Inorganic compounds contained in the sample (sulfate equivalent) | | The First Method in the Japanese Standards of Quasi-drug Ingredients 2006 (Japan) or JIS K0067-1992 |
| Ester value (mg KOH/g) | Ester bonds in lactone rings and acetyl groups | The amount (mg) of potassium hydroxide required for complete saponification of esters contained in 1 g of the sample | The JOCS Standard Methods for the Analysis of Fats, Oils and Related Materials (2.3.3-1996) defined by the Japan Oil Chemists' Society |

TABLE 10-continued

| Test item | Components to be measured | Measurement details | Method applied |
|---|---|---|---|
| Evaporation residue (%) | Mass measurement of coexisting substances (in particular, coexisting substances having a high boiling) point) in the sample | The amount (mass %) of the residue obtained through evaporation of the sample | The Second Method in JIS K0067-1992 |
| Drying loss (%) | Mass measurement of water and other volatile substances (low boiling-point compounds) contained in the sample | Loss (mass %) of the sample when it is dried | The First Method in JIS K0067-1992 (Method of heat-drying under atmospheric pressure) |
| Ethanol soluble matter (%) | Mass measurement of substances soluble in ethanol in the sample (polar substances such as surfactants) | Proportion (mass %) of ethanol-soluble components | JISK3362-2008 |
| Infrared absorption spectrum | —$CH_2$ and —$CH_3$ contained in alkyl chains in the sample, COOH bound to alkyl chains, and C—OH of glucose | Spectra of wavelengths absorbed when the sample is irradiated with electromagnetic waves in the infrared region | Infrared spectroscopy (ATR method) |

(2) Test Method
(A) Ignition Residue

The ignition residue test is a method of measuring the amount of residual substances after the sample is ignited by the method below (first method). This method is typically used to measure the amount of inorganic substances contained as impurities in an organic substance. This method may also be used to measure the amount of inorganic substances contained as components in an organic substance or the amount of impurities contained in a volatile inorganic substance. For example, in the present invention, "an ignition residue of 0.1% or less (the first method, 1 g)" means that when about 1 g of the sample was accurately measured and ignited according to the procedure of the first method described below, the residue of the sample after the ignition was 0.10% or less, based on the sampling amount.

Sampling Method

After a crucible made of platinum, quartz, or ceramics was ignited and allowed to cool in a desiccator (silica gel), the mass of the crucible was accurately measured. A predetermined amount of each sample was accurately weighed (within a measurement error range of ±10%) (sampling amount) into the crucible, and subjected to the following procedure.

First Method

On the crucible, after the sample was moistened with a small amount of sulfuric acid and subjected to gradual heating to ash or vaporize most of the sample at temperatures as low as possible, the sample was moistened with sulfuric acid, then completely ashed, and ignited (at 450 to 550° C.) until the weight became constant. After the residue was allowed to cool in a desiccator (silica gel), the mass was accurately measured. The ignition residue (%) was calculated from the obtained measurement value (residue) and the pre-measured sampling amount according to the formula below.

Ignition residue (%)=([W2−W3]/[W1−W3])×100  Mathematical Formula 5

W1: Mass (g) of the sample container (crucible) and the sampling amount
W2: Weight (g) of the sample container (crucible) and the residue
W3: Mass (g) of the sample container (crucible)

(B) Ester Value

The ester value can be determined as the difference between the saponification value (the amount (mg) of potassium hydroxide required to neutralize the free acids contained in 1 g of the sample and to saponify the ester contained in 1 g of the sample: JIS K 3331, the JOCS Standard Methods for the Analysis of Fats, Oils and Related Materials (2.3.1-1996)) and the acid value (the amount (mg) of potassium hydroxide required to neutralize the free acids contained in 1 g of the sample: JIS K 3331, the JOCS Standard Methods for the Analysis of Fats, Oils and Related Materials (2.3.1-1996)). Alternatively, as a direct measurement method, the following method can also be used.

Direct Method

About 3 g of the sample was accurately weighed into a saponification flask, and 50 mL of 95 vol % ethanol was added. Using a phenolphthalein indicator (the acid value was obtained), the sample was neutralized by titration with a 0.1 mol/L potassium hydroxide standard solution while swirling the flask well. Subsequently, 25 mL of a 0.5 mol/L of potassium hydroxide-ethanol standard solution was accurately added and a flask was equipped with a condenser. The flask was gently heated with occasional swirling, while adjusting the heating temperature so that the refluxing ethanol would not reach the upper end of the condenser. Immediately after the content of the flask was boiled for 30 minutes, the flask was cooled. The condenser was removed before the content was hardened into an agar-like state. Several drops of phenolphthalein indicator were added and titration was performed with a 0.5 mol/L hydrochloric acid standard solution. Thirty seconds after the disappearance of the slight crimson color of the indicator was defined as the terminal point, and the amount of the 0.5 mol/L hydrochloric acid standard solution required to reach this point was defined as "the amount (mL) of 0.5 mol/L hydrochloric acid standard solution used in the test." For comparison, a blank test was concurrently conducted by weighing 50 mL of 95 vol % ethanol into a flask and precisely adding 25 mL of the 0.5 mol/L hydrochloric acid standard solution. The amount of the 0.5 mol/L hydrochloric acid standard solution required in the blank test was defined as "the amount (mL) of the 0.5 mol/L hydrochloric acid standard solution used in the blank test." The ester value was calculated from the formula below.

$$\text{Ester value} = [28.05 \times (A-B) \times F]/C \quad \text{Mathematical Formula 6}$$

A: Amount (mL) of the 0.5 mol/L hydrochloric acid standard solution used in the blank test
B: Amount (mL) of the 0.5 mol/L hydrochloric acid standard solution used in the test
C: Sampling amount (g)
F: Factor of the 0.5 mol/L hydrochloric acid standard solution (C) Evaporation Residue
[Residue on Evaporation Test]

After being accurately weighed, the sample was evaporated to dryness according to the second method of JIS K0067-1992 (method of thermal evaporation on a hot plate), and the residue was weighed. The evaporation residue (%) was calculated according to the formula below.

$$\text{Evaporation residue (\%)} = ([W2-W3]/[W1-W3]) \times 100 \quad \text{Mathematical Formula 7}$$

W1: Mass (g) of the sample container and the sample
W2: Weight (g) of the sample container and the residue
W3: Mass (g) of the sample container (D) Drying Loss
[Drying Loss Test]

The sample was accurately weighed and then dried by heating (105±2° C., for 2 hours) according to the first method of JIS 0067-K1992 (a method of drying by heating under atmospheric pressure). The reduced amount of the sample after drying was weighed, and the drying loss (%) was calculated according to the formula below.

$$\text{Drying loss (\%)} = ([W1-W2]/[W1-W3]) \times 100 \quad \text{Mathematical Formula 8}$$

W1: Mass (g) of the weighing bottle and the sample before drying
W2: Mass (g) of the weighing bottle and the sample after drying
W3: Mass (g) of the weighing bottle (E) Ethanol Soluble Matter The "ethanol soluble matter" refers to the amount of substances dissolved in ethanol when ethanol was added to the sample.

[Measurement Method]

An Erlenmeyer flask and a glass filter were accurately weighed. The weights of these instruments were measured after being dried at 105° C. for at least 2 hours and allowed to cool in a desiccator. About 5 g of the sample was accurately weighed out to one milligram and placed into the Erlenmeyer flask. After 100 mL of ethanol was added to the sample, the flask was equipped with a glass tube and heated on a water bath for 30 minutes with occasional swirling for dissolution. For powder or granular samples, 95 vol % ethanol was used. For liquid or paste samples, 99.5 vol % ethanol was used. After the warm solution, as is, was filtered through a glass filter, 50 mL of ethanol was added to the residue in the Erlenmeyer flask again to dissolve the residue. The resulting warm solution was filtered using a glass filter, and the Erlenmeyer flask and the glass filter were washed well with hot ethanol. After being allowed to cool to room temperature, the filtrate and the wash were transferred to a 250-mL volumetric flask, and ethanol was added to a marked line. Using a transfer pipette, 100-mL portions of the liquid were aliquoted into two 200-mL beakers with a known mass. One of the beakers was heated on a water bath and ethanol was removed. The residue was dried for 1 hour in a dryer adjusted to 105±2° C., allowed to cool in a desiccator, and then accurately weighed.

Ethanol soluble matter was calculated according to the formula below.

$$\text{Ethanol soluble matter (mass \%)} = (A/[S \times 100/250]) \times 100 \quad \text{Mathematical Formula 9}$$
$$= ([250 \times A]/S)$$

A: Amount (g) of the dry residue
S: Mass (g) of the sample
(F) Infrared Absorption Spectrum The liquid sample was used after being dried to a solid by heating at 105±2° C. for 3 hours. The solid sample was used as is. The infrared absorption spectrum was analyzed by the ATR method using a Fourier transform infrared spectrometer Spectrum™100 (produced by PerkinElmer Co., Ltd.).

(3) Test Results

The above test results are shown in the Table below.

TABLE 11

| Test item | Example product 2 | Example product 4 | Reference Production Example 1 | Comparative Example 2 |
| --- | --- | --- | --- | --- |
| Ignition residue (%) | 0 | 0.5 | 0.1 | 38.4 |
| Ester value (mg KOH/g) | 1 | 6 | 102 | 9 |
| Evaporation residue (%) | 100 | 99 | 59 | 90 |
| Drying loss (%) | 0 | 1 | 41 | 10 |
| Ethanol soluble matter (%) | 100 | 99 | 59 | 71 |
| Absorption peak of the infrared absorption spectrum ($cm^{-1}$) | 1024, 1706, 2854, 2924, 3000-3500 | 1024, 1706, 2854, 2924, 3000-3500 | 1024, 1741, 2854, 2924, 3000-3500 | 1024, 1724, 2854, 2924, 3000-3500 |

As is clear from the results, the high purity acid-form SL-containing compositions of the present invention (Example product 2 and Example product 4) have an ignition residue of 0 to 30% and an ester value of 0 to 20 mgKOH/g, and are significantly different in these points from Reference Production Example product 1 (a lactone-form/acid-form SL-containing composition) and Comparative Example product 2 (a partially purified acid-form SL-containing composition).

Furthermore, the high purity acid-form SL-containing compositions (Example products 2 and 4) of the present invention have an evaporation residue of 91 to 100%, a drying loss of 0 to 9%, and an ethanol soluble matter of 80 to 100%, and are also significantly different in these points from Reference Example product 1 and Comparative Example product 2.

Further, the infrared absorption spectra of high purity acid-form SL-containing compositions of the present invention (Example product 2 and Example product 4) have an absorption peak at 1706 cm$^{-1}$. In contrast, the infrared absorption spectra of Reference Production Example product 1 and Comparative Example product 2 do not have an absorption peak corresponding thereto. Thus, the high purity acid-form SL-containing compositions of the present invention are different also in this point from the conventional acid-form SL-containing compositions.

Test Example 3

Investigation of Gelling Conditions of the Acid-Form Sophorolipid

As shown in Example 4, acid-form SL gels upon refrigeration under acidic conditions. In this test, gelling conditions (pH, temperature) were investigated.
(1) Test Method
The acid-form SL-containing composition (Reference Production Example product 2) (25 g) prepared in Reference Production Example 2 was adjusted to a pH of 2 to 7 (pH 2, 3, 4, 5, 6, 7) using a 62.5% sulfuric acid aqueous solution. Ten grams each of the thus prepared liquids were weighed into test tubes, respectively. These test tubes were stored at −25° C. to 20° C., and the elapsed time and changes in appearance (liquid state) were recorded.
(2) Test Results
The results are shown in the Table below.

TABLE 12

| Temperature (° C.) | Elapsed time (day) | pH | | | | | |
|---|---|---|---|---|---|---|---|
| | | 2 | 3 | 4 | 5 | 6 | 7 |
| 20 | 3 | − | − | − | − | − | − |
| 15 | 1 | ± | ± | ± | − | − | − |
| | 2 | ± | ± | ± | − | − | − |
| 10 | 1 | + | + | + | − | − | − |
| | 2 | + | + | + | ± | − | − |
| −10 | 1 | + | + | + | ± | ± | − |
| −15 | 1 | + | + | + | + | ± | − |
| −20 | 1 | + | + | + | + | ± | ± |
| −25 | 1 | + | + | + | + | + | + |

−: Liquid,
±: Partially gelled
+: Gelled

As is clear from the Table, when the temperature was 20° C., the acid-form SL-containing composition was in a liquid state at any pH and did not gel. When the temperature was 15° C. or 10° C., the acid-form SL-containing composition started to gel at pH 2 to 4. At pH 5 to 7, the acid-form SL-containing composition started to gel at 10° C. or lower, and more preferably −10° C. or lower. When the temperature was −25° C., the acid-form SL-containing composition was gelled and solidified at any pH. These suggest the following gelling conditions. Under highly acidic conditions of pH 2 to 4, the temperature may be 15° C. or lower, and preferably 10° C. or lower. Under mildly acidic conditions of higher than pH 4 and not higher than pH 6, the temperature may be 10° C. or lower, and preferably −10° C. Under mildly acidic conditions of higher than pH 6 and not higher than pH 7, the temperature may be −20° C. or lower.

When acid-form SL gel is washed with water and purified as shown in Example 4, temperature conditions are preferably 0° C. or higher to avoid the freezing of the water. Accordingly, the pH condition for gelling is preferably pH 4 or lower at which acid-form SL gels at 0° C. or higher.

Test Example 4

Lotions were prepared according to the formulations shown in the Table below using Example product 2, Reference Production Example product 1, and Comparative Example product 2 (samples 1 to 5). After observing the pH, odor, and appearance, the samples were subjected to a stability test. The stability test was performed by observing changes in appearance after storage under thermostatic conditions of 50° C. (in the dark) for 1 month. In each test, five panelists performed evaluations according to the following criteria, and the answer given the highest number of times was used as the test result.

Odor

A: No irritative odor

B: An irritative odor

Stability Over Time

A: No change in appearance

B: Slight separation, precipitation, etc.

C: Complete separation

Table 13 shows the results.

TABLE 13

| | | | | | (Parts by weight) |
|---|---|---|---|---|---|
| | Sample No. | | | | |
| | 1 | 2 | 3 | 4 | 5 |
| Example product 2 | 0.1 | 0.5 | 1.0 | — | — |
| Reference Example product 1 | — | — | — | 0.1 | — |
| Comparative Example product 2 | — | — | — | — | 0.1 |
| Glycerol | 5.0 | 5.0 | 5.0 | 5.0 | 5.0 |

TABLE 13-continued

| | Sample No. | | | | (Parts by weight) |
|---|---|---|---|---|---|
| | 1 | 2 | 3 | 4 | 5 |
| Phenoxyethanol | 1.0 | 1.0 | 1.0 | 1.0 | 1.0 |
| 49% potassium hydroxide (pH adjuster) | Appropriate amount | Appropriate amount | Appropriate amount | Appropriate amount | Appropriate amount |
| Water | Balance | Balance | Balance | Balance | Balance |
| Total (parts by weight) | 100 | 100 | 100 | 100 | 100 |
| pH | 6.0 | 6.0 | 6.0 | 6.0 | 6.0 |
| Odor | A | A | A | B | B |
| Appearance | Transparent | Transparent | Transparent | Transparent | Transparent |
| Stability over time | A | A | A | A | A |

Glycerin (concentrated glycerin, ACIDCHEM)
Phenoxyethanol (Phenoxyethanol S, produced by Dai-ichi Kogyo Seiyaku Co., Ltd.)

As shown in Table 13, all of the lotions (samples 1 to 5) prepared using Example product 2, Reference Production Example product 1, and Comparative Example product 2 were transparent in appearance and stable over time. However, the lotions (samples 4 and 5) prepared using Reference Production Example product 1 and Comparative Example product 2 were odorous (had an irritative odor), whereas the lotions (samples 1 to 3) prepared using Example product 2 of the present invention were odorless (had no irritative odor).

Test Example 5

Emulsions were prepared according to the formulations shown in the Table below using Example product 2, polyglyceryl-10 laurate, Reference Production Example product 1, and Comparative Example product 2. The pH, odor, and appearance of the lotions were observed and a stability test (50° C. for 7 days) was also performed in the same manner as in Test Example 4. Polyglyceryl-10 laurate is a surfactant having HLB similar to that of the acid-form SL of Example product 2 (powder).

The appearance was evaluated according to the following criteria. Odor and stability over time were evaluated according to the same criteria as in Test Example 4.

Appearance
A: No milky white color, oil droplets, or separation was observed.
B: Milky white color and oil droplets were observed.
C: Completely separated.

TABLE 14

| | Sample No. | | | | | | | |
|---|---|---|---|---|---|---|---|---|
| | 6 | 7 | 8 | 9 | 10 | 11 | 12 | 13 |
| Example product 2 | 1.0 | 1.0 | 0.5 | 1.0 | 1.0 | 3.0 | — | — |
| Polyglyceryl laurate | — | — | — | — | — | — | 1.0 | — |
| Production Example product 1 | — | — | — | — | — | — | — | 1.0 |
| Comparative Example product 2 | — | — | — | — | — | — | — | — |
| Hydrogenated lecithin | 0.1 | 0.1 | 0.1 | 0.1 | 0.1 | 0.1 | 0.1 | 0.1 |
| Squalane | 1.0 | 2.0 | — | — | — | 1.0 | — | 1.0 |
| Jojoba oil | — | — | 1.0 | 1.0 | — | — | 1.0 | — |
| Macadamia nut oil | — | — | — | — | 1.0 | — | — | — |
| 1,3-butylene glycol | 5.0 | 5.0 | 5.0 | 5.0 | 5.0 | 5.0 | 5.0 | 5.0 |
| Phenoxyethanol | 1.0 | 1.0 | 1.0 | 1.0 | 1.0 | 1.0 | 1.0 | 1.0 |
| 49% potassium hydroxide (PH adjuster) | q.s. | q.s. | q.s. | q.s. | q.s. | q.s. | q.s. | q.s. |
| Water | Balance | Balance | Balance | Balance | Balance | Balance | Balance | Balance |
| Total | 100 | 100 | 100 | 100 | 100 | 100 | 100 | 100 |
| pH | 6.0 | 6.0 | 6.0 | 6.0 | 6.0 | 6.0 | 6.0 | 6.0 |
| Odor | A | A | A | A | A | A | A | C |
| Appearance | A | A | A | A | A | Transparent | A | C |
| Stability over time | B | B | B | B | A | B | C | C |

TABLE 14-continued

| | Sample No. | | | | | | |
|---|---|---|---|---|---|---|---|
| | 14 | 15 | 16 | 17 | 18 | 19 | 20 |
| Example product 2 | — | — | — | — | — | — | — |
| Polyglyceryl laurate | — | — | — | — | — | — | — |
| Production Example product 1 | 3.0 | 1.0 | 1.0 | — | — | — | — |
| Comparative Example product 2 | — | — | — | 1.0 | 3.0 | 1.0 | 1.0 |
| Hydrogenated lecithin | 0.1 | 0.1 | 0.1 | 0.1 | 0.1 | 0.1 | 0.1 |
| Squalane | 1.0 | — | — | 1.0 | 1.0 | — | — |
| Jojoba oil | — | 1.0 | — | — | — | 1.0 | — |
| Macadamia nut oil | — | — | 1.0 | — | — | — | 1.0 |
| 1,3-butylene glycol | 5.0 | 5.0 | 5.0 | 5.0 | 5.0 | 5.0 | 5.0 |
| Phenoxyethanol | 1.0 | 1.0 | 1.0 | 1.0 | 1.0 | 1.0 | 1.0 |
| 49% potassium hydroxide (PH adjuster) | q.s. | q.s. | q.s. | q.s. | q.s. | q.s. | q.s. |
| Water | Balance | Balance | Balance | Balance | Balance | Balance | Balance |
| Total | 100 | 100 | 100 | 100 | 100 | 100 | 100 |
| pH | 6.0 | 6.0 | 6.0 | 6.0 | 6.0 | 6.0 | 6.0 |
| Odor | C | C | C | C | C | C | C |
| Appearance | C | C | C | C | B | A | A |
| Stability over time | C | C | C | C | C | C | A |

Polyglyceryl laurate-10 (HLB 15.5) (Decaglun 1-L, produced by Nikko Chemicals Co., Ltd.)
Hydrogenated lecithin (Lecinol S-10, produced by Nikko Chemicals Co., Ltd.)
Squalane (NIKKOL Squalane, produced by Nikko Chemicals Co., Ltd.)
Jojoba oil (NIKKOL Jojoba Oil, produced by Nikko Chemicals Co., Ltd.)
*Macadamia* nut oil (NIKKOL Macadamia Nut Oil, produced by Nikko Chemicals Co., Ltd.)
1,3-butylene glycol (produced by Daicel Chemical Industries, Ltd.)
Phenoxyethanol (Phenoxyethanol S, produced by Dai-ichi Kogyo Seiyaku Co., Ltd.)

It was found that emulsions (samples 13 to 20) prepared using Reference Production Example product 1 and Comparative Example product 2 had an irritative odor and had poor stability over time. In contrast, emulsions (samples 6 to 11) prepared using Example product 2 had no irritative odor and had improved stability over time. Further, emulsions (samples 6 to 11) prepared using Example product 2 exhibited better stability over time than the emulsion (sample 12) prepared using polyglyceryl-10 laurate that is generally used as an emulsifier.

Test Example 6

Using Example product 2, Example product 4, Reference Production Example product 1, and Comparative Example product 2, 100 g of emulsions were produced according to the formulations shown in Table 10. 40 g each of the emulsions was transferred to two round measuring standard vials (Model No. 10), and one of the two vials was allowed to stand in a dark place at room temperature (25±5° C.) for 1 day and the other was allowed to stand in a dark place at 50° C. for 1 day. After the 1 day of standing, the standard vials were agitated gently in such a manner that the vials were turned upside down, and emulsion stability was evaluated based on the appearance thereafter. Oleoresin paprika 10000 CV incorporated as a component is an oil-soluble dye. Accordingly, if coalescence in an emulsion forms an oil layer, the oil layer appears orange in color. That is, if emulsion stability is low, an orange oil layer is formed on the surface. Accordingly, the emulsion stability was evaluated according to the following criteria.

Emulsion Stability

A: No orange oil droplets or orange oil layer was observed on the surface.

B: Although no oil layer was confirmed on the surface, a small number of orange oil droplets were observed.

C: An orange oil layer was observed on the surface.

TABLE 15

(Parts by weight)

| | Sample No. | | | |
|---|---|---|---|---|
| | 21 | 22 | 23 | 24 |
| Example product 2 | 1 | — | — | — |
| Example product 4 | — | 1 | — | — |
| Reference Production Example product 1 | — | — | 1 | — |
| Comparative Example product 2 | — | — | — | 1 |
| Hydrogenated lecithin | 0.1 | 0.1 | 0.1 | 0.1 |
| Squalane | 1 | 1 | 1 | 1 |
| 1,3-Butylene glycol | 5 | 5 | 5 | 5 |
| Oleoresin paprika 10000CV | 0.01 | 0.01 | 0.01 | 0.01 |
| Distilled water | Balance | Balance | Balance | Balance |

TABLE 15-continued

| | (Parts by weight) Sample No. | | | |
|---|---|---|---|---|
| | 21 | 22 | 23 | 24 |
| 49% potassium hydroxide (pH adjuster) | q.s. | q.s. | q.s. | q.s. |
| Phenoxyethanol | 1 | 1 | 1 | 1 |
| Total | 100 | 100 | 100 | 100 |
| pH | 6.0 | 6.0 | 6.0 | 6.0 |
| Emulsion stability | A | B | C | C |

Oleoresin paprika 10000CV (produced by Kobe Chemical Co., Ltd.)

When the emulsions (samples 23 and 24) prepared in Reference Production Example products 1 and 2 were used, an orange oil layer was confirmed. This indicates a loss of emulsion stability and the occurrence of coalescence. These phenomena occurred presumably because Reference Production Example product 1 has an ester value of greater than 20 mgKOH/g and lacks uniformity as a sophorolipid molecular assembly and because Comparative Example product 2 had an ignition residue of more than 30%, which tends to cause coalescence within the emulsion. In contrast, no oil layer was confirmed in the emulsions (samples 21 and 22) prepared in Example products 2 and 4. It was confirmed that the emulsions (samples 21 and 22) have improved emulsion stability compared to samples 23 and 24.

Test Example 7

Using Example product 2, Reference Production Example product 1, and Comparative Example product 2, creams were prepared according to the formulations shown in Table 16 below. Using the same methods and criteria as in Test Examples 4 to 6, odor and appearance were observed and a stability test (50° C. for 1 month) was performed.

TABLE 16

| | (Parts by weight) Sample No. | | | |
|---|---|---|---|---|
| | 21 | 22 | 23 | 24 |
| Example product 2 | 1.0 | 1.0 | — | — |
| Reference Production Example 1 | — | — | 1.0 | — |
| Comparative Example product 2 | — | — | — | 1.0 |
| Hydrogenated lecithin | 0.01 | 0.01 | 0.01 | 0.01 |
| Squalane | 0.5 | 0.5 | 0.5 | 0.5 |
| Jojoba oil | 1.0 | 1.0 | 1.0 | 1.0 |
| Shea fat | 1.0 | 1.0 | 1.0 | 1.0 |
| 1,3-Butylene glycol | 5.0 | 5.0 | 5.0 | 5.0 |
| Glycerol | 5.0 | 5.0 | 5.0 | 5.0 |
| Carbomer | 0.1 | 0.1 | 0.1 | 0.1 |
| Acrylic acid/alkyl acrylate ($C_{10-30}$) copolymer | 0.1 | 0.1 | 0.1 | 0.1 |
| Xanthan gum | 0.04 | 0.04 | 0.04 | 0.04 |
| Phenoxyethanol | 1.0 | 1.0 | 1.0 | 1.0 |
| 49% potassium hydroxide (pH adjuster) | q.s. | q.s. | q.s. | q.s. |
| Distilled water | Balance | Balance | Balance | Balance |
| Total | 100 | 100 | 100 | 100 |
| pH | 6.0 | 6.0 | 6.0 | 6.0 |
| Odor | A | A | C | C |
| Appearance | B | A | B | B |
| Emulsion stability | A | A | A | A |

Hydrogenated lecithin (Lecinol S-10, produced by Nikko Chemicals Co., Ltd.)
Squalane (NIKKOL Squalane, produced by Nikko Chemicals Co., Ltd.)
Jojoba oil (NIKKOL Jojoba Oil, produced by Nikko Chemicals Co., Ltd.)
Shea fat (Cropure Shea Butter-SO-, produced by Croda Japan K.K.)
1,3-Butylene glycol (produced by Daicel Chemical Industries, Ltd.)
Carbomer (Carbopol 980, produced by Nikko Chemicals Co., Ltd.)
Acrylic acid/alkyl acrylate ($C_{10-30}$) copolymer (PEMULEN TR-1, produced by Daicel Chemical Industries, Ltd.)
Xanthan gum (Keltrol T, produced by Dainippon Sumitomo Pharma Co., Ltd.)
Phenoxyethanol (Phenoxyethanol S, produced by Dai-ichi Kogyo Seiyaku Co., Ltd.)

The above results indicate that none of the creams (samples 21 and 22) prepared using Example product 2 had an irritative odor and that the creams were stable even after storage for one month.

INDUSTRIAL APPLICABILITY

According to the production method of the present invention, a highly pure acid-form sophorolipid can be prepared safely with less energy using a simple method. Since the high-purity acid-form sophorolipid-containing composition of the present invention does not have undesirable odors, particularly an irritative odor caused by acetic acid, the composition can be suitably applied to food products, cosmetics, medications, etc.

The invention claimed is:
1. A method for producing an acid-form sophorolipid-containing composition, the method comprising the following steps (i-b) and (ii-b):
   (i-b) adjusting the pH of a partially purified acid-form sophorolipid-containing composition to an acidic range of not higher than pH 4; and
   (ii-b) leaving the acidified partially purified acid-form sophorolipid-containing composition obtained in step (i) to stand under low-temperature conditions of not higher than 15° C. to acquire a resulting gelled object, and washing the gelled object with a cold solvent selected from water, ethanol, and a mixture thereof;
   wherein the composition has properties of the following (1), (2), (3), (6), and (7);
   (1) the composition amount of acetic acid contained per ml of a solution obtained by dissolving 1 g of an ethanol soluble matter of the composition in a 5% sulfuric acid aqueous solution to make a total volume of 3 ml being 5 μg/ml or less;
   (2) ignition residue: 0 to 10%;
   (3) ester value: 0 to 9 mg KOH/g;
   (6) ethanol soluble matter: 98 to 100%; and
   (7) a 15 mass% aqueous solution of the composition with a pH of 3 becomes a gel when cooled to 4° C.

2. The method according to claim 1, further comprising the following step before step (i-b):
   a step of subjecting a liquid culture of a sophorolipid-producing yeast or a processed product of the liquid culture to alkali hydrolysis to prepare a partially purified acid-form sophorolipid-containing composition with an acid-form sophorolipid content of 78 mass% or more, based on the total amount of sophorolipids.

3. The method according to claim 1, the method further comprising the following steps:
   (iii) distilling a liquid acid-form sophorolipid-containing composition obtained via steps (i-b) and (ii-b), and
   (iv) precipitating an acid-form sophorolipid from a residual liquid obtained from the distillation.

4. The method according to claim 3, wherein step (iv) is a step of spray-drying.

5. The method according to claim 1, the method further comprising the following steps:
   (v) solidifying, through cooling, an acid-form sophorolipid-containing composition obtained via steps (i-b) and (ii-b); and
   (vi) drying the cooling-solidified object.

6. The method according to claim 5, wherein the steps of (v) and (vi) are freeze-drying steps.

* * * * *